(12) United States Patent
Lee et al.

(10) Patent No.: US 7,198,790 B2
(45) Date of Patent: Apr. 3, 2007

(54) GROWTH DIFFERENTIATION FACTOR-5

(75) Inventors: Se-Jin Lee, Baltimore, MD (US);
Thanh Huynh, Baltimore, MD (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 0 days.

(21) Appl. No.: 09/880,708

(22) Filed: Jun. 12, 2001

(65) Prior Publication Data

US 2002/0165361 A1 Nov. 7, 2002

Related U.S. Application Data

(60) Continuation of application No. 09/145,060, filed on Sep. 1, 1998, now Pat. No. 6,245,896, which is a division of application No. 08/455,559, filed on May 31, 1995, now Pat. No. 5,801,014, which is a continuation-in-part of application No. PCT/US94/00657, filed on Jan. 12, 1994, which is a continuation-in-part of application No. 08/003,144, filed on Jan. 12, 1993, now abandoned.

(51) Int. Cl.
*A61K 39/395* (2006.01)
*G01N 33/548* (2006.01)
*C07K 16/22* (2006.01)

(52) U.S. Cl. .............. 424/145.1; 424/158.1; 424/178.1; 435/7.23; 435/7.9; 530/388.23; 530/389.2; 530/391.1; 530/391.3

(58) Field of Classification Search .......... 435/7.1, 435/7.23, 7.9, 7.92, 8; 530/387.1, 388.1, 530/388.23, 389.2, 391.3; 424/9, 130.1, 424/145.1, 158.1, 178.1
See application file for complete search history.

(56) References Cited

U.S. PATENT DOCUMENTS 4,741,998 A 5/1988 Herr et al.
5,061,786 A 10/1991 Burnier et al.

FOREIGN PATENT DOCUMENTS

WO WO 93/16099 8/1993

OTHER PUBLICATIONS

Nathan et al. Cytokines in context. Journal of Cell Biology, (Jun. 1991) 113 (5) 981-986.*
Hill et al. Bi-functional action of transforming growth factor-beta on DNA synthesis in early passage human fetal fibroblasts. J Cell Physiol Aug. 1986;128(2):322-8.*
Bowie et al., "Deciphering the message in protein sequences: Tolerance to amino acid substitutions," *Science* 247:1306-1310 (1990).
Daniel et al., *Virology* 202(2):540-549 (1994).
Lee, "Identification of a novel member (GDF-1) of the transforming growth factor-beta superfamily," *Molecular Endocrinology* 4(7):1034-1040 (1990).
Wang et al., "Recombinant human bone morphogenetic protein induces bone formation," *Proc. Natl. Acad. Sci. USA* 87(6):2220-2224 (1990).
Wozney et al., "Novel regulators of bone formation: molecular clones and activities," *Science* 242:1528-1534 (1988).

* cited by examiner

*Primary Examiner*—David Romeo
(74) *Attorney, Agent, or Firm*—DLA Piper US LLP

(57) ABSTRACT

Growth differentiation factor-5 (GDF-5) is disclosed along with its polynucleotide sequence and amino acid sequence. Also disclosed are diagnostic and therapeutic methods of using the GDF-5 polypeptide and polynucleotide sequences.

11 Claims, 11 Drawing Sheets

```
   1  TTCAAGCCCTCAGTCAGTTGTGCGGGAGAAAGGGGGCGGTCGGCTTTCTCCTTTCAAGAA   60
  61  CGAGTTATTTCAGCTGCTGCTGGAGAGACGGTGCACGTCTGGACACACTCAGACTTCCAC  120
 121  TATGGGACTGGATACAGACACACGCCCGGCGACTTCAAGACGCTGCTGAAGACCACTCCTT  180
 181  GCCCTGCCGCTGCTGCTGCCAAGCCAGAGGCCACCTTCGCTGCTACGGCCTTTCTCTGGTGT  240
 241  TCATGGTTTTCCTGCCAAGCCAGAGGATGAGACTCCCCAAACTCCTCACTCTTTGTGTGGCAC  300
 301  CATTCAGCGGCTGCTGGCCAGAGGATGAGACTCCCCAAACTCCTCACTCTTTGTGTGGCAC  360
          M  R  L  P  K  L  T  L  L  W  H
 361  CTGGCTTGGCTGGACTGGAACTCATCTGCACTGTGCTGGGTGCCCCTGACTTAGGACAG   420
      L  A  W  L  D  L  E  L  I  C  T  V  L  G  A  P  D  L  G  Q
 421  AGAACCCCAGGGCCAAGCCAGGTTGACCAAGGCCGAGGCCAAGGAGAGGCCACCCCTG    480
      R  T  P  G  A  K  P  G  L  T  K  A  E  K  E  R  P  P  L
 481  GCCAGGAATGTCTTTAGGCCAGGGGTCATATCTATGGTGTGGGGGCCACCAATGCCAGG   540
      A  R  N  V  F  R  P  G  H  I  Y  G  V  G  A  T  N  A  R
 541  GCCAAGGGAAGCTCTGGGCAGACAGGCCAAGACCCAGGAGAACCCAGAAGATGCCCCCC    600
      A  K  G  S  S  G  Q  T  Q  A  K  K  D  E  P  R  K  M  P  P
 601  AGATCCGGTGCTCTGAAACCAAGCCAGGACCCTCTTCCCAGACTAGACAGGCTGCAGCC   660
      R  S  G  S  E  T  K  P  G  P  S  S  Q  T  R  Q  A  A  A
 661  CGGACTGTAACCCAAAGACACAGCTTCCTGGGGCAAAGCATCTTCAAAGCAGGATCT    720
      R  T  V  T  P  K  G  Q  L  P  G  G  K  A  S  S  K  A  G  S
 721  GCCCCCAGCTCCTTCCTGCTGAAGAAGACCAGGAAGACCTGGAGCCTCGAGAGCCCAAG   780
      A  P  S  S  F  L  L  K  K  T  R  E  P  G  T  P  R  E  P  K
 781  GAGCCGTTCCGCCCCCCCATCACACCCCACGAATACATGCTCTCCCTGTACAGGACG     840
      E  P  F  R  P  P  P  I  T  P  H  E  Y  M  L  S  L  Y  R  T
 841  CTGTCCGATGCTGACAGAAAGGGAGGTAACAGCAGCGTGAAGTTGGAGGCTGGCCTGGCC   900
      L  S  D  A  D  R  K  G  G  [N  S  S] V  K  L  E  A  G  L  A
 901  AACACCATCACCAGCTTTATTGACAAGGGCAAGATGGGCCTTGGGGGCTGAACTG       960
      N  T  I  T  S  F  I  D  K  G  Q  D  D  R  G  P  A  V  R  K
 961  CAGAGGTACGTGTTTGACATCAGTGCCTTGGAGAAGGATGGGCTTGGGCTGAACTG    1020
      Q  R  Y  V  F  D  I  S  A  L  E  K  D  G  L  L  G  A  E  L
1021  CGGATCTTACGGAAGAAGCCCTTGGACGTGGCCAAGCCCGGCAGTAGCGGGCGG       1080
      R  I  L  R  K  K  P  L  D  V  A  K  P  A  V  P  S  S  G  R
1081  GTTGCCCAACTGAAGCTGTCCAGTGCCCAGCGCCAGCCGGCAGCCTTGCTGGAT       1140
      V  A  Q  L  K  L  S  S  C  P  S  G  R  Q  P  A  A  L  L  D
```

FIG. 2A

```
1141 GTGCGCTCCGTGCCAGGCCTGGATGGATCTGGCTGGAGGTGTTCGACATCTGGAAGCTC   1200
      V  R  S  V  P  G  L  D  G  S  G  W  E  V  F  D  I  W  K  L
1201 TTCCGAAATTTTAAGAACTCAGCGGCAGTGCCTGGGAGCCTGGAGGCCTGGAACGGGGC   1260
      F  R  N  F  K  N  S  A  Q  L  C  L  E  L  E  A  W  E  R  G
1261 CGGGCCGTGGACCTCCGTGGCTTTGAACGCACTGCCCGACAGGTCCACGAGAAA       1320
      R  A  V  D  L  R  G  L  G  F  E  R  T  A  R  Q  V  H  E  K
1321 GCCTGTGTTCCTAGTGTTTGGTCGTACCAAGAAACGGGACCTGTTCTTTAATGAGATTAAG  1380
      A  L  F  L  V  F  G  R  T  K  K  R  D  L  F  F  N  E  I  K
1381 GCCCGTCTGGCCAGGATGACAAGACTGTATGAATATTTGTTCAGCCAGGCGGAA        1440
      A  R  S  G  Q  D  D  K  T  V  Y  E  Y  L  F  S  Q  R  R  K
1441 CGCCGGGCCCCATTGGCCAATCGCCAGGCAAGAACCTCAAGGCTCGC              1500
      R  R  A  P  L  A  N  R  Q  G  K  R  P  S  K  N  L  K  A  R
1501 TGCAGTCGCAAGGCCTTGCATGTCAACTTCAAGGACATGGGCTGTGAGTTCCCCTTGGCTCC  1560
      C  S  R  K  A  L  H  V  N  F  K  D  M  G  W  D  D  W  I  I
1561 GCACCTCTTGAGTATGAGGCCCACAAACCAGTCATTCAGCCTATTAGCATCCTCTTCATC  1620
      A  P  L  E  Y  E  A  F  H  C  E  G  L  C  E  F  P  L  R  S
1621 CACTTGGAGCCCACAAACCACGCAGTCATTCAGACTCTGATGAACTCTATGGACCCTGAA  1680
      H  L  E  P  T  N  H  A  V  I  Q  T  L  M  N  S  M  D  P  E
1681 TCCACACCACCACCACTTGTTGTGCCTACACGGCTGAGTCCTATTAGCATCCTCTTCATC  1740
      S  T  P  P  T  C  C  V  P  T  R  L  S  P  I  S  I  L  F  I
1741 GACTCTGCCAACAACGTGGTGTATAAACAGTACGAGGACATGGTCGTGAATCTGTGGC   1800
      D  S  A  N  N  V  V  Y  K  Q  Y  E  D  M  V  E  S  C  G
1801 TGCAGGTAGCAGCACCGGCCCACTGTCTTCCCAGGTGGCACATCCAGAGACTACCCCCT  1860
      C  R  *
1861 CTACAGGTTCCTGAGTAACAGAGAGCCTGCTGCCCGAAGTTCCTGGCAGC           1920
1921 CTGCAGGAAAGAGTTCTCAGCAGGCTTCTCTCGATGATCTGGACTAAAGAGATCA      1980
1981 CCTTCTGAAGATTCCTGCCAAGAACATCTGAGTGGGCCTCAGGAAAGGT            2040
2041 GTTCTTAATGAGATTCAGAGAAGTTGTAGAGAAGTTGCCGAGAGAGAGCCTTCATTTCTCT  2100
2101 CCAGACTCTCCAGAGAAGTTGTAGAGAAGTTGCCGAGATGTTCATTACAGGGCTGTCCT   2160
2161 CCTTGAATCACCTTTGTCTGGTGACTTTCTGCCAGAGATGTTCATTACAGGGCTGG     2220
2221 GCAAAGAGGGAAAGGCTTGGCAGGGGTGAAGAAGCTATGAGCCTAATTAGACT         2280
2281 GTTAGATTAAAATGTACATCGATGACATAAAAAGCTGAATCTTCATGGCT    2329
```

|          |       | 371                                                                                                        395         |
|----------|-------|------------------------------------------------------------------------------------------------------------------------|
| SEQ ID NO:28 | GDF-5 | R K R R A P L A N — R Q G K R P S — — — — — — — — — — — — — — — — — — — — — — K N L K A R C S |
| SEQ ID NO:29 | GDF-6 | R R R R T A F A S R H G K R H G — — — — — — — — — — — — — — — — — — — — — — — K K S R L R C S |
| SEQ ID NO:30 | GDF-7 | R R R R T A L A G T R G A Q G S G G G G G G G G G G G G G G G A G R G H G R R G R S R C S |

|       | 396                                                                                                        446 |
|-------|--------------------------------------------------------------------------------------------------------------|
| GDF-5 | R K A L H V N F K D M G W D D W I I A P L E Y E A F H C E G L C E F P L R S H L E P T N H A V I Q T L |
| GDF-6 | R K P L H V N F K E L G W D D W I I A P L E Y E A Y H C E G V C D F P L R S H L E P T N H A I I Q T L |
| GDF-7 | R K S L H V D F K E L G W D D W I I A P L D Y E A Y H C E G V C D F P L R S H L E P T N H A I I Q T L |

|       | 447                                                                                                        495 |
|-------|--------------------------------------------------------------------------------------------------------------|
| GDF-5 | M N S M D P E S T P P T C C V P T R L S P I S I L F I D S A N N V V Y K Q Y E D M V V E S C G C R |
| GDF-6 | M N S M D P G S T P P S C C V P T K L T P I S I L Y I D A G N N V V Y K Q Y E D M V V E S C G C R |
| GDF-7 | L N S M A P D A A P A S C C V P A R L S P I S I L Y I D A A N N V V Y K Q Y E D M V V E A C G C R |

GROWTH DIFFERENTIATION FACTOR-5

This application is a continuation application of prior U.S. application Ser. No. 09/145,060, filed Sep. 1, 1998, issued Jun. 12, 2001 as U.S. Pat. No. 6,245,896; which is a divisional application of U.S. application Ser. No. 08/455,559, filed May 31, 1995, issued Sep. 1, 1998 as U.S. Pat. No. 5,801,014; which is a continuation-in-part application of PCT/US94/00657, filed Jan. 12, 1994; which is a continuation-in-part of U.S. application Ser. No. 08/003,144, filed Jan. 12, 1993, now abandoned; all of the disclosures of which are incorporated herein by reference in their entirety.

BACKGROUND OF THE INVENTION

1. Field of the Invention

The invention relates generally to growth factors and specifically to a new member of the transforming growth factor beta (TGF-β) superfamily, which is denoted, growth differentiation factor-5 (GDF-5).

2. Description of Related Art

The transforming growth factor β (TGF-β) superfamily encompasses a group of structurally-related proteins which affect a wide range of differentiation processes during embryonic development. The family includes, Mullerian inhibiting substance (MIS), which is required for normal male sex development (Behringer et al., Nature 345:167, 1990), Drosophila decapentaplegic (DPP) gene product, which is required for dorsal-ventral axis formation and morphogenesis of the imaginal disks (Padgett, et al., Nature, 325:81–84, 1987), the Xenopus Vg-1 gene product, which localizes to the vegetal pole of eggs ((Weeks, et al., Cell, 51:861–867, 1987), the activins (Mason, et al., Biochem. Biophys. Res. Commun., 135:957–964, 1986), which can induce the formation of mesoderm and anterior structures in Xenopus embryos (Thomsen et al., Cell 63:485, 1990), and the bone morphogenetic proteins (BMPs, osteogenin, OP-1) which can induce de novo cartilage and bone formation (Sampath, et a., J. Biol. Chem. 265: 13198, 1990). The TGF-βs can influence a variety of differentiation processes, including adipogenesis, myogenesis, chondrogenesis, hematopoiesis, and epithelial cell differentiation (for review, see Massague, Cell 49:437, 1987).

The proteins of the TGF-β family are initially synthesized as a large precursor protein which subsequently undergoes proteolytic cleavage at a cluster of basic residues approximately 110–140 amino acids from the C-terminus. The C-terminal regions of the proteins are all structurally related and the different family members can be classified into distinct subgroups based on the extent of their homology. Although the homologies within particular subgroups range from 70% to 90% amino acid sequence identity, the homologies between subgroups are significantly lower, generally ranging from only 20% to 50%. In each case, the active species appears to be a disulfide-linked dimer of C-terminal fragments. For most of the family members that have been studied, the homodimeric species has been found to be biologically active, but for other family members, like the inhibins (Ling, et al., Nature 321:779, 1986) and the TGF-βs (Cheifetz, et al., Cell, 48:409, 1987), heterodimers have also been detected, and these appear to have different biological properties than the respective homodimers.

Identification of new factors that are tissue-specific in their expression pattern will provide a greater understanding of that tissue's development and function.

SUMMARY OF THE INVENTION

The present invention provides a cell growth and differentiation factor, GDF-5, a polynucleotide sequence which encodes the factor and antibodies which are immunoreactive with the factor. This factor appears to relate to various cell proliferative disorders, especially those involving the uterus, such as endometriosis and uterine tumors, and those involving skeletal tissues.

Thus, in one embodiment, the invention provides a method for detecting a cell proliferative disorder of uterine origin and which is associated with GDF-5. In another embodiment, the invention provides a method of treating a cell proliferative disorder associated with expression of GDF-5, by suppressing or enhancing GDF-5 activity.

BRIEF DESCRIPTION OF THE DRAWINGS

FIGS. 2A AND 2B show the nucleotide (SEQ ID NO:9) and predicted amino acid (SEQ ID NO:10) sequences of GDF-5. The putative tetrabasic processing sites are dented by stippled boxes.

FIG. 3A shows the alignment of the C-terminal sequences of GDF-5 (SEQ ID NO:13) with other members of the TGF-β family (SEQ ID NOS: 11, 12, and 14 to 27, respectively). The conserved cysteine residues are shaded. Dashes denote gaps introduced in order to maximize alignment.

FIG. 3B shows alignment of GDF-5, GDF-6 and GDF-7 C-terminal amino acids.

FIG. 6 shows portions of the skeletons of transgenic mice stained with alizarin red.

DETAILED DESCRIPTION OF THE INVENTION

Figures 1A, 1B:
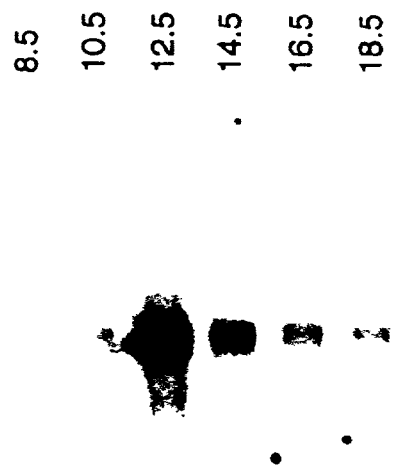
FIG. 1A shows expression of GDF-5 mRNA in adult tissues.
FIG. 1B shows expression of GDF-5 mRNA in embryonic tissues.

The present invention provides a growth and differentiation factor, GDF-5 and a polynucleotide sequence encoding GDF-5. Unlike other members of the TGF-β superfamily, GDF-5 expression is highly tissue specific, being expressed in cells primarily in uterine tissue and skeletal tissue. In one embodiment, the invention provides a method for detection of a cell proliferative disorder of the uterus or skeletal tissue such as bone or cartilage, which is associated with GDF-5 expression. In another embodiment, the invention provides a method for treating a cell proliferative disorder associated with expression of GDF-5 by using an agent which suppresses or enhances GDF-5 activity.

The TGF-β superfamily consists of multifunctional polypeptides that control proliferation, differentiation, and other functions in many cell types. Many of the peptides have regulatory effects, both positive and negative, on other peptide growth factors. The structural homology between the GDF-5 protein of this invention and the members of the TGF-β family, indicates that GDF-5 is a new member of the family of growth and differentiation factors. Based on the known activities of many of the other members, it can be expected that GDF-5 will also possess biological activities that will make it useful as a diagnostic and therapeutic reagent.

The expression of GDF-5 in the uterus suggests a variety of applications using the polypeptide, polynucleotide, and antibodies of the invention, related to contraception, fertility, pregnancy, and cell proliferative diseases. Abnormally low levels of the factor may be indicative of impaired function in the uterus while abnormally high levels may be indicative of hypertrophy, hyperplasia, or the presence of ectopic tissue. Hence, GDF-5 may be usefull in detecting not only primary and metastatic neoplasms of uterine origin but in detecting diseases such as endometriosis as well. In addition, GDF-5 may also be useful as an indicator of developmental anomalies in prenatal screening procedures.

The expression of GDF-5 during embryogenesis and specifically in the precartilaginous mesenchyme associated with early bone formation in the limbs, suggests a variety of applications using the polypeptide, polynucleotide, and antibodies of the invention, related to skeletal development, cartilage differentiation, and cell proliferative diseases. Abnormally low or high levels of GDF-5 may be indicative of various bone dysplasias such as epiphyseal, physeal (growth plate), metaphyseal and diaphyseal hypo- and hyperplasias. Examples of such diseases which may be diagnosed and/or treated rising GDF-5 polynucleotides and antibodies include: spondyloepiphyseal dysplasia, dysplasia epiphysialis hemimelica, achondroplasia, metaphyseal dysostosis, hyperchondroplasia, enchondromatosis, hypophosphatasia, osteopetrosis, craniometaphyseal dysplasia, osteogenesis imperfecta, idiopathic osteoporosis, Engelman's disease and hyperphosphatasia (See Harrison's Principles of Internal Medicine, McGraw-Hill Book Co., N.Y., 1987, Chpt. 339). The induction of bone formation by GDF-5 is illustrated in Example 4.

Several members of the TGF-β superfamily possess activities suggesting possible applications for the treatment of cell proliferative disorders, such as cancer. In particular, TGF-β has been shown to be potent growth inhibitor for a variety of cell types (Massague, *Cell* 49:437, 1987), MIS has been shown to inhibit the growth of human endometrial carcinoma tumors in nude mice (Donahoe, et al., *Ann. Surg.* 194:472, 1981), and inhibin αhas been shown to suppress the development of tumors both in the ovary and in the testis (Matzuk, et al., *Nature,* 360:313, 1992). GDF-5 may have a similar activity and may therefore be useful as an antiproliferative agent, such as for the treatment of endometrial cancer or endometriosis.

Many of the members of the TGF-β family are also important mediators of tissue repair. TGF-β has been shown to have marked effects on the formation of collagen and causes of striking angiogenic response in the newborn mouse (Roberts, et a., *Proc. Natl. Acad. Sci., USA* 83:4167, 1986). The BMP's can induce new bone growth and are effective for the treatment of fractures and other skeletal defects (Glowacki, et al, *Lancet,* 1:959, 1981; Ferguson, et al., *Clin. Orthoped. Relat. Res,* 227:265, 1988; Johnson, et al., *Clin Orthoped. Relat. Res.,* 230:257, 1988). Sequence homology and expression data together suggest that GDF-5 may have similar activities and may be useful in repair of tissue injury caused by trauma or bums for example. GDF-5 may play a role in regulation of the menstrual cycle or regulation of uterine function during pregnancy, and therefore, GDF-5, anti-GDF-5 antibodies, or antisense polynucleotides may be useful either in contraceptive regimens, in enhancing the success of in vitro fertilization procedures, or in preventing premature labor.

The term "substantially pure" as used herein refers to GDF-5 which is substantially free of other proteins, lipids, carbohydrates or other materials with which it is naturally associated. One skilled in the art can purify GDF-5 using standard techniques for protein purification. The substantially pure polypeptide will yield a single major band on a non-reducing polyacrylamide gel. The purity of the GDF-5 polypeptide can also be determined by amino-terminal amino acid sequence analysis. GDF-5 polypeptide includes functional fragments of the polypeptide, as long as the activity of GDF-5 remains. Smaller peptides containing the biological activity of GDF-5 are included in the invention.

The invention provides polynucleotides encoding the GDF-5 protein. These polynucleotides include DNA, cDNA and RNA sequences which encode GDF-5. It is understood that all polynucleotides encoding all or a portion of GDF-5 are also included herein, as long as they encode a polypeptide with GDF-5 activity. Such polynucleotides include naturally occurring, synthetic, and intentionally manipulated polynucleotides. For example, GDF-5 polynucleotide may be subjected to site-directed mutagenesis. The polynucleotide sequence for GDF-5 also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of GDF-5 polypeptide encoded by the nucleotide sequence is functionally unchanged.

The polynucleotide encoding GDF-5 includes SEQ ID NO:9 as well as nucleic acid sequences complementary to SEQ ID NO:9. A complementary sequence may include an antisense nucleotide. When the sequence is RNA, the deoxynucleotides A, G, C, and T of SEQ ID NO:9 is replaced by ribonucleotides A, G, C, and U, respectively. Also included in the invention are fragments of the above-described nucleic acid sequences that are at least 15 bases in length, which is sufficient to permit the fragment to selectively hybridize to DNA that encodes the protein of SEQ ID NO:10 under physiological conditions. Specifically, the fragments should hybridize to DNA encoding GDF-5 protein under stringent conditions.

Specifically disclosed herein is a cDNA sequence for GDF-5 which is 2329 base pairs in length and contains an open reading frame beginning with a methionine codon at nucleotide 322. The encoded polypeptide is 495 amino acids in length with a molecular weight of about 54.9 K, as determined by nucleotide sequence analysis. The GDF-5 sequence contains a core of hydrophobic amino acids near the N-terminus, suggestive of a signal sequence for secretion. GDF-5 contains one potential N-glycosylation sites at amino acid 183 and two putative tetrabasic proteolytic processing sites RRKRR and KR-at amino acids 371–375 and amino acids 384–385. Cleavage of the precursor at these sites would generate mature C-terminal fragments of 120 or 110 amino acids in length with predicted molecular weights of 13.6K and 12.5K, respectively.

GDF-5 contains all of the highly conserved residues present in other family members, including the seven cysteine residues with their characteristic spacing. Among the known family members, GDF-5 is most highly related to BMP-2 and BMP4 in the C-terminal portion of the molecule (57% amino acid sequence identity calculated from the first conserved cysteine).

Minor modifications of the recombinant GDF-5 primary amino acid sequence may result in proteins which have substantially equivalent activity as compared to the GDF-5 polypeptide described herein. Such modifications may be deliberate, as by site-directed mutagenesis, or may be spontaneous. All of the polypeptides produced by these modifications are included herein as long as the biological activity of GDF-5 still exists. Further, deletion of one or more amino acids can also result in a modification of the structure of the resultant molecule without significantly altering its biological activity. This can lead to the development of a smaller active molecule which would have broader utility. For example, one can remove amino or carboxy terminal amino acids which are not required for GDF-5 biological activity.

The nucleotide sequence encoding the GDF-5 polypeptide of the invention includes the disclosed sequence and conservative variations thereof The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

DNA sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences and 2) antibody screening of expression libraries to detect cloned DNA fragments with shared structural features.

Preferably the GDF-5 polynucleotide of the invention is derived from a mammalian organism, and most preferably from a mouse, rat, or human. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.*, 9:879, 1981).

The development of specific DNA sequences encoding GDF-5 can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of MRNA is eventually formed which is generally referred to as cDNA.

Of the three above-noted methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay et al., *Nucl. Acid Res.* 11:2325, 1983).

A cDNA expression library, such as lambda gt11, can be screened indirectly for GDF-5 peptides having at least one epitope, using antibodies specific for GDF-5. Such antibodies can be either polyclonally or monoclonally derived and used to detect expression product indicative of the presence of GDF-5 cDNA.

DNA sequences encoding GDF-5 can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the GDF-5 polynucleotide sequences may be inserted into a recombinant expression vector. The term "recombinant expression vector" refers to a plasmid, virus or other vehicle known in the art that has been manipulated by insertion or incorporation of the GDF-5 genetic sequences Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg et al., *Gene* 56:125, 1987), the pMSXND expression vector for expression in mammalian cells (Lee and Nathans, *J. Biol. Chem.* 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

Polynucleotide sequences encoding GDF-5 can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaC_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the GDF-5 of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, *Eukaryotic Viral Vectors*, Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

The invention includes antibodies immunoreactive with GDF-5 polypeptide or functional fragments thereof. Antibody which consists essentially of pooled monoclonal antibodies with different epitopic specificities, as well as distinct monoclonal antibody preparations are provided. Monoclonal antibodies are made from antigen containing fragments of the protein by methods well known to those skilled in the art (Kohler, et al., *Nature,* 256:495, 1975). The term antibody as used in this invention is meant to include intact molecules as well as fragments thereof, such as Fab and $F(ab')_2$, which are capable of binding an epitopic determinant on GDF-5.

The term "cell-proliferative disorder" denotes malignant as well as non-malignant cell populations which often appear to differ from the surrounding tissue both morphologically and genotypically. The GDF-5 polynucleotide that is an antisense molecule is usefull in treating cell proliferative disorders of the various organ systems, particularly, for example, the uterus or skeletal system. Cell proliferative disorders of the skeletal system include those disorders of bone cells and cartilage as described above. Essentially, any disorder involving cells that are normally responsive to GDF-5 could be considered susceptible to treatment with a GDF-5 suppressing reagent.

The invention provides a method for detecting a cell proliferative disorder of the uterus or skeletal system (e.g., bone, cartilage) which comprises contacting an anti-GDF-5 antibody with a cell suspected of having a GDF-5 associated disorder and detecting binding to the antibody. The antibody reactive with GDF-5 is labeled with a compound which allows detection of binding to GDF-5. For purposes of the invention, an antibody specific for GDF-5 polypeptide may be used to detect the level of GDF-5 in biological fluids and tissues. Any specimen containing a detectable amount of antigen can be used. A preferred sample of this invention is tissue of uterine origin, specifically endometrial tissue or skeletal tissue such as bone and cartilage. The level of GDF-5 in the suspect cell can be compared with the level in a normal cell to determine whether the subject has a GDF-5-associated cell proliferative disorder. Preferably the subject is human.

The antibodies of the invention can be used in any subject in which it is desirable to administer in vitro or in vivo immunodiagnosis or immunotherapy. The antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA) and the sandwich (immunometric) assay. Detection of the antigens using the antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The antibodies of the invention can be bound to many different carriers and used to detect the presence of an antigen comprising the polypeptide of the invention. Examples of well-known carriers include class, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or will be able to ascertain such, using routine experimentation.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific antihapten antibodies.

In using the monoclonal antibodies of the invention for the in vivo detection of antigen, the detectably labeled antibody is given a dose which is diagnostically effective. The term "diagnostically effective" means that the amount of detectably labeled monoclonal antibody is administered in sufficient quantity to enable detection of the site having the antigen comprising a polypeptide of the invention for which the monoclonal antibodies are specific.

The concentration of detectably labeled monoclonal antibody which is adminstered should be sufficient such that the binding to those cells having the polypeptide is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. Such dosages may vary, for example, depending on whether multiple injections are given, antigenic burden, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that deleterious radiation with respect to the host is minimized. Ideally, a radioisotope used for in vivo imaging will lack a particle emission, but produce a large number of photons in the 140–250 keV range, which may readily be detected by conventional gamma cameras.

For in vivo diagnosis radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The monoclonal antibodies of the invention can be used in vitro and in vivo to monitor the course of amelioration of a GDF-5-associated disease in a subject. Thus, for example, by measuring the increase or decrease in the number of cells expressing antigen comprising a polypeptide of the invention or changes in the concentration of such antigen present in various body fluids and tissues, it would be possible to determine whether a particular therapeutic regimen aimed at ameliorating the GDF-5-associated disease is effective. The term "ameliorate" denotes a lessening of the detrimental effect of the GDF-5-associated disease in the subject receiving therapy.

The present invention identifies a nucleotide sequence that can be expressed in an altered manner as compared to expression in a normal cell, therefore it is possible to design appropriate therapeutic or diagnostic techniques directed to this sequence. Thus, where a cell-proliferative disorder is associated with the expression of GDF-5, nucleic acid sequences that interfere with GDF-5 expression at the translational level can be used. This approach utilizes, for example, antisense nucleic acid and ribozymes to block translation of a specific GDF-5 mRNA, either by masking that mRNA with an antisense nucleic acid or by cleaving it with a ribozyme.

Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded.

Antisense oligomers of about 15 nucleotides are preferred, since they are easily synthesized and are less likely to cause problems than larger molecules when introduced into the target GDF-5-producing cell. The use of antisense methods to inhibit the in vitro translation of genes is well known in the art (Marcus-Sakura, *Anal. Biochem.*, 5 172: 289, 1988).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.*, 260:3030, 1988). A major advantage of this approach is that, because they are sequence-specific, only mRNAs with particular sequences are inactivated.

There are two basic types of ribozymes namely, tetrahymena-type (Hasselhoff, *Nature*, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The present invention also provides gene therapy for the treatment of cell proliferative disorders which are mediated by GDF-5 protein. Such therapy would achieve its therapeutic effect by introduction of the GDF-5 antisense polynucleotide into cells having the proliferative disorder. Delivery of antisense GDF-5 polynucleotide can be achieved using a recombinant expression vector such as a chimeric virus or a colloidal dispersion system. Especially preferred for therapeutic delivery of antisense sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaiMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a GDF-5 sequence of interest into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the GDF-5 antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to Ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for GDF-5 antisense polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are usefull as delivery vehicles in vitro and in vivo. It has been shown that large unilamellar vesicles (LUV), which range in size from 0.2–4.0 μm can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

The following examples are intended to illustrate but not limit the invention. While they are typical of those that might be used, other procedures known to those skilled in the art may alternatively be used.

EXAMPLE 1

Identification and Isolation of a Novel TGF-β Family Member

To identify a new member of the TGF-β superfamily, degenerate oligonucleotides were designed which corresponded to two conserved regions among the known family members: one region spanning the two tryptophan residues conserved in all family members except MIS and the other region spanning the invariant cysteine residues near the C-terminus. These primers were used for polymerase chain reactions on mouse genomic DNA followed by subcloning the PCR products using restriction sites placed at the 5' ends of the primers, picking individual *E. coli* colonies carrying these subcloned inserts, and using a combination of random sequencing and hybridization analysis to eliminate known members of the superfamily.

GDF-5 was identified by polymerase chain reaction (PCR) using mouse genomic DNA with the following primers:

SJL 136: 5'-CCGGAATTCGG(G/A/T/C)TGGGA(G/A)(A/C)G(G/A/T/C)TGG(G/A)T (G/A/T/C)(G/A)T-3' (SEQUENCE D NO. 1)

SJL 121: 5'-CCGGAATTC(G/A)CAICC(G/A)CA(T/C)TC (G/A)TCIACIACCAT(G/A) TC(T/C)TC(G/A)TA-3' (SEQUENCE ID NO. 2)

SJL 136 corresponds to the amino acid sequence GWE(R/S)W(V/I/M) (V/I/M), (SEQUENCE ID NO. 3) and the complement of SJL 121 corresponds to the amino acid sequence YEDMVVDECGC (SEQUENCE ID NO. 4). Both oligonucleotide sets were designed to contain an EcoRI restriction site at the 5' end to facilitate subcloning. PCR was carried out for 40 cycles at 94° C. for 1', 50° C. for 2' and 72° C. for 3.5'.

Human GDF-5 was isolated by PCR using human genomic DNA with the following primers:

SJL 141: 5'-CCGGAATTCGGITGG(G/C/A)A(G/A/T/C) (A/G)A(T/C)TGG(A/G) TI(A/G)TI(T/G)CICC-3' (SEQUENCE D NO. 5)

SJL 145: 5' -CCGGAATTC(G/A)CAI(G/C)C(G/A)CAIG (C/A)(G/A/T/C)TCIACI(G/A) (T/C)CAT-3' (SEQUENCE ID NO. 6)

SSJL 141 corresponds to the amino acid sequence GW(H/Q/N/K/D/E)(D/N)W-(V/I/M)(V/I/M)(A/S)P (SEQUENCE D NO. 7) and the complement of SJL 145 corresponds to the amino acid sequence M(V/I/M/T/A)V(D/E)(A/S)C(G/A)C (SEQUENCE ID NO. 8). Both the oligonucleotide sets were designed to contain an EcoRI restriction site at the 5' end to facilitate subcloning. PCR was carried out for 40 cycles at 94° C. for 1 min., 50° C. for 2 min., and 72° C. for 2 min. Partial sequence analysis of the human PCR product revealed no predicted amino acid differences between mouse and human GDF-5.

PCR products of approximately 280 bp were gel-purified, digested with Eco RI, gel-purified again, and subcloned in the Bluescript vector (Stratagene, San Diego, Calif.). Bacterial colonies carrying individual subclones were picked into 96 well microtiter plates, and multiple replicas were prepared by plating the cells onto nitrocellulose. The replicate filters were hybridized to probes representing known members of the family, and DNA was prepared from non-hybridizing colonies for sequence analysis.

RNA isolation and Northern analysis were carried out as described previously (Lee, S. J., *Mol. Endocrinol.* 4:1034, 1990). An oligo dT-primed cDNA library was prepared from 2.5–3 µg of 12.5 day gestation CD-1 mouse embryo poly A-selected RNA in the lambda ZAP II vector according to the instructions provided by Stratagene. The library was amplified prior to screening. Filters were hybridized as described previously (Lee, S.-J., *Proc. Natl. Acad. Sci. USA.*, 88:4250–4254, 1991). DNA sequencing of both strands was carried out using the dideoxy chain termination method (Sanger, et al., *Proc. Natl. Acad. Sci., USA* 74:5463–5467, 1977) and a combination of the S1 nuclease/exonuclease III strategy (Henikoff, S., *Gene,* 28:351–359, 1984) and synthetic oligonucleotide primers.

EXAMPLE 2

Expression Pattern and Sequence of GDF-5

To determine the expression pattern of GDF-5, RNA samples prepared from a variety of adult tissues were screened by Northern analysis. RNA isolation and Northern analysis were carried out as described previously (Lee, S. J., *Mol. Endocrinol,* 4:1034, 1990). Five micrograms of twice polyA-selected RNA prepared from each tissue were electrophoresed on formaldehyde gels, blotted and probed with GDF-5. As shown in FIG. 1A, the GDF-5 probe detected an approximately 2.5 kb mRNA expressed primarily in the uterus and at lower levels in other adult tissues in the mouse, including placenta, brain, thymus, lung, kidney, and adrenal gland. The GDF-5 probe also detected a larger mRNA in the oviduct. High levels of GDF-5 transcripts were also detected in mouse embryos, particularly at day 12.5 of gestation (FIG. 1B).

A CD-1 day 12.5 whole mouse embryo cDNA library was constructed in lambda ZAP II and screened with a probe derived from the GDF-5 PCR product. The nucleotide sequence (SEQ ID NO:9) of the longest hybridizing clone is shown in FIG. 2. The in-frame termination codons upstream of the putative initiating ATG and the consensus polyadenylation signals are underlined. The poly A tails are not shown. Numbers indicate nucleotide position relative to the 5' end. The 2329 bp sequence (SEQ ID NO:9) contains a long open reading frame (SEQ ID NO:10) beginning with a methionine codon at nucleotide 322 and potentially encoding a protein 495 amino acids in length with a molecular weight of 54.9 K. Like other TGF-β family members, the GDF-5 sequence contains a core of hydrophobic amino acids near the N-terminus suggestive of a signal sequence for secretion. GDF5 contains a single potential N-glycosylation sites at asparagine residue 183 (denoted by the plain box) and two putative tetrabasic proteolytic processing sites at amino acids 371–375 (denoted by the stippled box) and amino acids 384–385 (SEQ ID NO:10). GDF-5 contains all of the highly conserved residues present in other family members (FIGS. 3 {SEQ ID NOS:11 to 27, respectively} and 4), including the seven cysteine residues with their characteristic spacing. Among the known mammalian family members, GDF-5 (SEQ ID NO:13) is most highly related to BMP-2 (SEQ ID NO:15) and BMP-4 (SEQ ID NO:16) in the C-terminal portion of the molecule (57% amino acid sequence identity calculated from the first conserved cysteine).

Figure 3A:
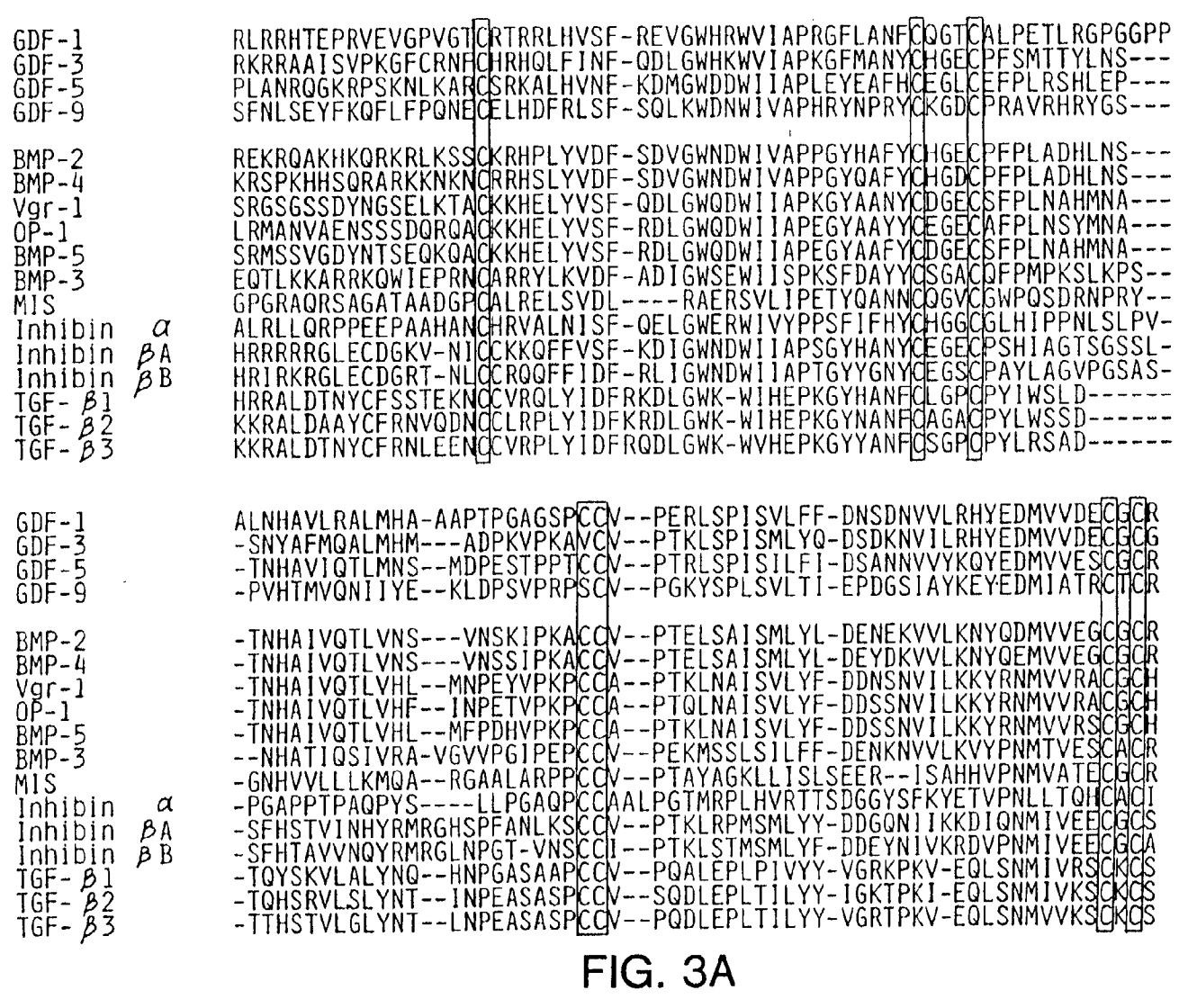

Although the C-terminal portion of GDF-5 clearly shows homology with the other family members, the sequence of GDF-5 is significantly diverged from those of the other family members (FIGS. 3 {SEQ ID NOS:11 to 27, respectively} and 4). FIG. 3 shows the alignment of the C-terminal sequences of GDF-5 with the corresponding regions of human GDF-1 (SEQ ID NO:11 Lee, Proc. Natl. Acad. Sci. USA 88:4250–4254, 1991), human Vgr-1 (SEQ ID NO:17; Celeste, et al., Proc. Natl. Acad. Sci. USA 87:9843–9847, 1990), human OP-1 SEQ ID NO:18; Ozkaynak, et al., EMBO J. 9:2085–2093, 1990), human BMP-5 (SEQ ID NO:19; Celeste, et al., Proc. Natal. Acad. Sci. USA 87:9843–9847, 1990), human BMP-3 (SEQ ID NO:20; Wozney, et al., Science 242:1528–1534, 1988), human MIS (SEQ ID NO:21; Cate, et al. Cell, 45:685–698, 1986), human inhibin α, βA, and βB (SEQ ID NOS:22, 23 and 24, respectively; Mason, et al., Biochem, Biophys. Res. Commun., 135:957–964, 1986), human TGF-β1 (SEQ ID NO:25; Derynck, et al., Nature, 316:701–705, 1985), human TGF-β2 (SEQ ID NO:26; deMartin, et al., EMBO J., 6:36733677, 1987), human TGF-β3 (SEQ ID NO:27; ten Dijke, et al., Proc. Natl. Acad. Sci. USA 85:4715–4719, 1988), chicken TGF-β4 (Jakowlew, et al., Mol. Endocrinol. 2:1186–1195, 1988), and *Xenopus* TGF-β5 (Kondaiah, et al., J. Biol. Chem. 265:1089–1093, 1990). The conserved cysteine residues are boxed. Dashes denote gaps introduced in order to maximize the alignment.

Figure 4:
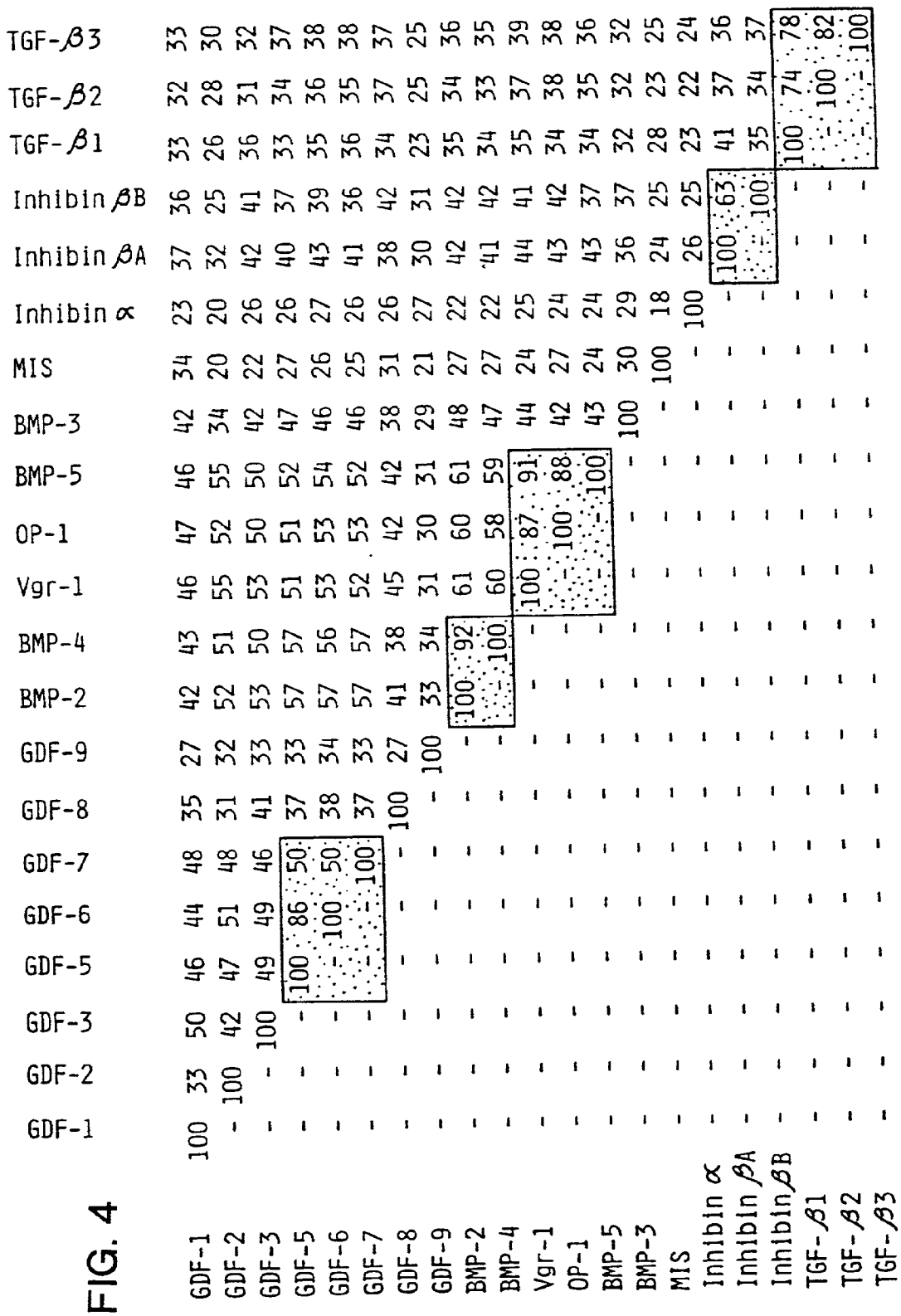
FIG. 4 shows amino acid homologies among the different members of the TGF-β superfamily. Numbers represent percent amino acid identities between each pair calculated from the first conserved cysteine to the C-terminus. Boxes represent homologies among highly-related members within particular subgroups.
Figure 5A:
FIG. 5 shows shows the expression of GDF-5 in limb mesenchyme of day 12.5 p.c. mouse embryos. Bright field (FIGS. 5a, 5d) and dark field (FIGS. 5b, 5c, 5e, 5f) photomicrographs of transverse (FIG. 5a–c) and sagittal (FIG. 5d–f) sections, showing views through forelimb and posterior end of embryo, respectively, after hybridization with $^{35}$S-labelled GDF-5 antisense strand (FIG. 5a,b,d,e) or sense strand control (FIGS. 5c, 5f) probes. Anterior (A), posterior (P), dorsal (D) and ventral (V) orientations are indicated.
Figure 5B:
Figure 5C:
Figure 5D:
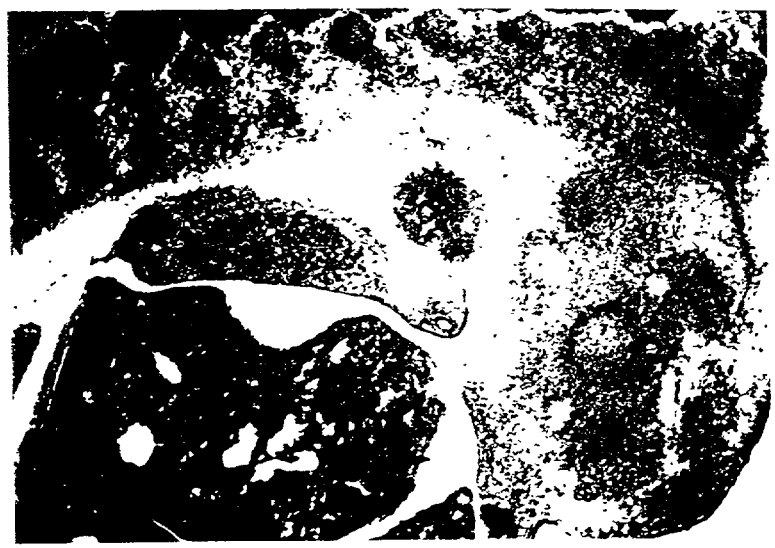
Figure 5E:
Figure 5F:

FIG. 4 shows the amino acid homologies among the different members of the TGF-β superfamily. Numbers represent percent amino acid identities between each pair calculated from the first conserved cysteine to the C-terminus. Boxes represent homologies among highly-related members within particular subgroups.

The degree of sequence identify with known family members ranges from a minimum of 24% with inhibin alpha to a maximum of 57% with BMP-2 and BMP4. GDF-5 shows no significant sequence homology to other family members in the pro-region of the molecule.

EXAMPLE 3

Expression of GDF-5 in Embryonic Tissue

The results in Example 2 show that during the development of the mouse embryo, the expression of GDF-5 begins at approximately day 10.5 post coitum (p.c.) and peaks at day 12.5 p.c., as indicated by the presence of a 2.5 kilobase (kb) major transcript (FIG. 1B). Of the adult mouse tissues examined, uterus contained the highest level of the 2.5 kb transcript, while low levels were detected in placenta (day 10.5 p.c.), oviduct, brain, thymus, heart, lung, kidney and adrenal gland (FIG. 1A). In oviduct tissue, the GDF-5 probe also detected a larger transcript of approximately 3.6 kb. GDF-5 transcripts were also detected by Northern blot analysis in femur and calvaria of newborn mice.

In order to characterize in more detail, the expression of GDF-5 in embryonic tissues, $^{35}$S-labelled probes synthesized from a portion of the cDNA clone encoding the relatively nonconserved prepro-region were hybridized in situ to serial sections of day 12.5 p.c. embryos. Day 12.5 p.c. female CD-1 mouse embryos were fixed and embedded in paraffin as described (Jones, C. M., et al., *Development*, 111:531–542, 1991). $^{35}$S-labelled antisense or sense strand RNA probes were synthesized by in vitro transcription from a template containing nucleotides 308 through 1446 of the GDF-5 cDNA clone (FIG. 2). Eight micron sections were hybridized with antisense or sense strand probe at 4×10$^5$ counts per minute/µl essentially as described (Jones, C. M., et al, supra) except that the proteinase K and acetic anhydride treatments were omitted, washes in 50% fromamide, 2×SSC, 0.1 M DTT were carried out at 65° C., and the final wash in 0.1×SSC was carried out at 37° C. Slides were developed after a 4–6 week exposure time with Kodak NTB3 emulsion and were stained with hematoxylin and eosin.

FIG. 5 shows shows the expression of GDF-5 in limb mesenchyme of day 12.5 p.c. mouse embryos. Bright field (FIG. 5*a*, 5*d*) and dark field (FIGS. 5*b*, 5*c*, 5*e*, 5*f*) photomicrographs of transverse (FIG. 5*a–c*) and sagittal (FIG. 5*d–f*) sections, showing views through forelimb and posterior end of embryo, respectively, after hybridization with $^{35}$S-labelled GDF-5 antisense strand (FIG. 5*a,b,d,e*) or sense strand control (FIGS. 5*c*, 5*f*) probes. Serial sections revealed hybridization to be localized to proximal (closed arrows) and distal (open arrows) mesenchyme in the forelimb (FIG. 5*a–c*) and hindlimb (FIG. 5*d–f*) Anterior (A), posterior (P), dorsal (D) and ventral (V) orientations are indicated.

GDF-5 transcripts were detected in both proximal and distal precartilaginous mesenchyme of the forelimbs and hindlimbs (FIG. 5). No other major sites of hybridization in the embryo were detected. The development of the long bones of the limbs begins with the condensation of mesenchyme, which differentiates into cartilage-forming cells. Osteogenic cells eventually invade the cartilage matrix and produce a bone matrix which becomes ossified (Rosen, V., et al., *Trends Genet.*, 8:97–102, 1992). In the mouse embryo at 12.5 days p.c., cartilage formation is just beginning in the long bones, and no sign of ossification is yet seen (Kaufman, M. H., *The Atlas of Mouse Development*, Academic Press, Inc., 1992). The peak of GDF-5 expression at this stage (FIG. 1B) and its primary location in the precartilaginous limb mesenchyme suggest that GDF-5 may affect the production, proliferation, and/or differentiation of the mesenchyme cells.

EXAMPLE 4

Induction of Bone Formation in Transgenic Mice Expressing GDF-5

In order to determine the biological activity of GDF-5 in vivo, transgenic mice were constructed that express GDF-5 ectopically. The GDF-5 coding sequence was cloned into the pMSXND expression vector (Lee and Nathans, *J. Biol. Chem.*, 263:3521–3527, 1988), and the metallothionein promoter/GDF-5 cassette was gel-purified and used to generate transgenic mice by standard methods known in the art. All injections and implantations were carried out by the transgenic mouse facility at the Johns Hopkins University School of Medicine.

Figure 6A:
FIGS. 6a and 6b show the lower limb of a mouse from one transgenic line.
Figure 6B:
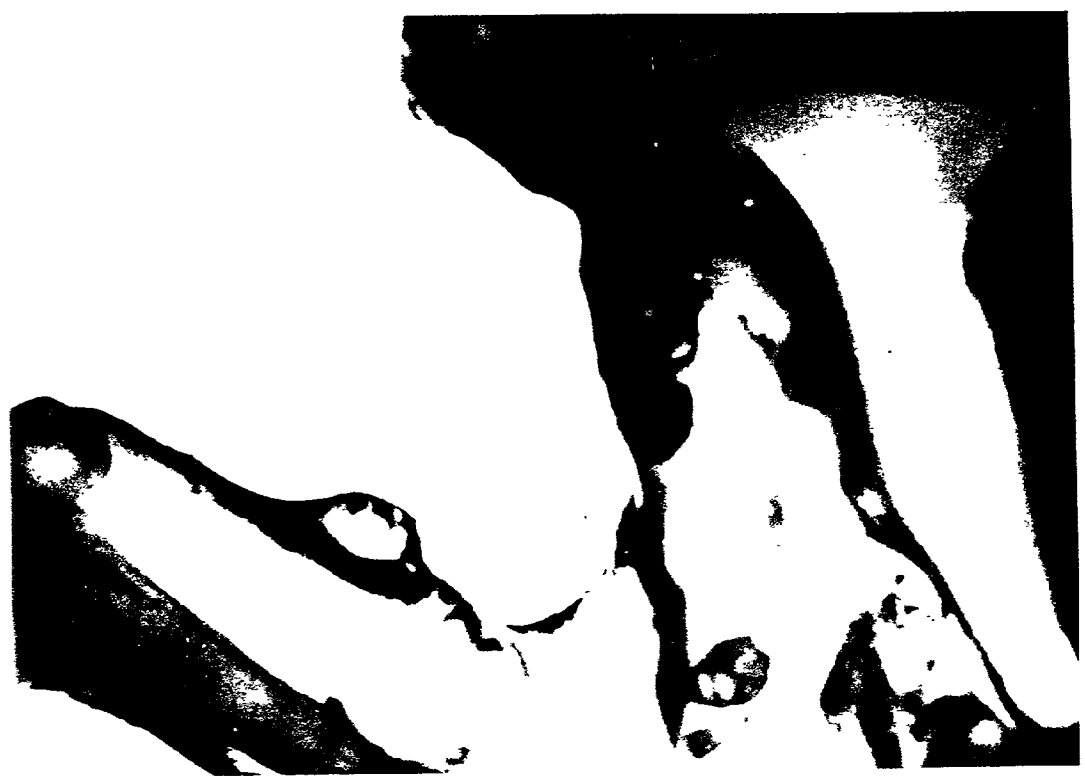
Figure 6C:
FIG. 6c shows the region behind the neck of a mouse from a second transgenic line.

Analysis of two independent transgenic mouse lines showed that these animals have ectopic bone formation. FIG. 6 shows portions of the skeletons of transgenic mice stained with alizarin red. FIGS. 6*a* and 6*b* show the lower limb of an animal from one transgenic line, and FIG. 6*c* shows the region behind the neck of an animal from a second transgenic line. In both animals, ectopic formation of bone within muscle tissue is evident. Hence, GDF-5 is capable of inducing bone formation in vivo.

In addition to GDF-5, two other members of the TGF-β superfamily have been suggested to play a role in limb development. In particular, BMP-2 and BMP4 are known to be expressed in the apical ectodermal ridge (AER) during mid-gestation at day 10.5 p.c. (Lyons, K. M., et al, *Development*, 109:833–844, 1990; Jones, C. M., et al., *Development*, 111:531–542, 1991). BMP-2 has been shown to inhibit the proliferation of mesenchyme cells in cultured limbs of mid-gestational embryos from which the AER had been removed (Niswander, L., et al., *Nature*, 361:68–71, 1993). Because BMP-2 and BMP-4 are also known to be expressed in limb mesenchyme at day 12.5 p.c. and because the active form of growth factors in this family is generally a disulfied-linked dimer, the possibility exists that homodimers or heterodimers of GDF-5, BMP-2 and BMP-4 may have distinct roles in limb development.

So far, the only bone morphogenetic protein for which mutants have been found is BMP-5, encoded by the mouse short ear locus (Kingsley, D. M., et al., *Cell*, 71:399–419, 1992). Mice homozygous for the short ear mutation, which causes a range of skeletal defects, have alterations in the size of shape of precartilaginous condensations of mesenchyme (Green, E. L., et al., *J. Morphol.*, 70:1–19, 1942). Skeletal defects of the limbs and digits may be caused by mutations in the mouse gene encoding GDF-5. Like BMP-5, GDF-5 controls particular aspects of skeletal morphology during development.

Although the invention has been described with reference to the presently preferred embodiment, it should be understood that various modifications can be made without departing from the spirit of the invention. Accordingly, the invention is limited only by the following claim.

What is claimed:

1. A method of detecting expression of growth differentiation factor-5 (GDF-5) in a tissue specimen of a subject, comprising contacting an antibody that specifically binds a GDF-5 polypeptide having the amino acid sequence as set forth in SEQ ID NO: 10 or SEQ ID NO: 13, or an antigen binding fragment of the antibody, with a tissue specimen of the subject, and detecting binding of the antibody or the antigen binding fragment of the antibody, wherein the specimen is from uterine neoplasm tissue or skeletal tissue.

2. The method of claim 1, wherein the detecting is in vivo.

3. The method of claim 1, wherein the detection is in vitro.

4. The method of claim 1, wherein the antibody is detectably labeled.

5. The method of claim 4, wherein the detectable label is a radioisotope, a fluorescent compound, a bioluminescent compound, a chemiluminescent compound, an enzyme, a colloidal metal, a phosphorescent compound, or a paramagnetic isotope.

6. The method of claim 1, wherein the antibody comprises a hapten coupled thereto.

7. The method of claim 6, wherein the hapten is biotin, dinitrophenyl, puridoxal, or fluorescein.

8. The method of claim 1, wherein the antibody is a monoclonal antibody.

9. The method of claim 1, wherein the antigen binding fragment of the antibody is a Fab fragment or an F(ab')₂ fragment.

10. The method of claim 1, wherein the antibody or antigen binding fragment of the antibody is bound to a solid phase carrier.

11. The method of claim 10, wherein the solid phase carrier comprises glass, polystyrene, polypropylene, polyethylene, dextran, nylon, amylase, natural cellulose, modified cellulose, polyacrylamide, agarose or magnetite.

* * * * *

SEQUENCE LISTING (1) GENERAL INFORMATION:

(iii) NUMBER OF SEQUENCES: 28

(2) INFORMATION FOR SEQ ID NO: 1:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: Genomic DNA (vii) IMMEDIATE SOURCE:
        (B) CLONE: 136

(xi) SEQUENCE DESCRIPTION: SEQ ID NO: 1:

CCGGAATTCG GNTGGGARMG NTGGRTNR                                            28

(2) INFORMATION FOR SEQ ID NO: 2:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: Genomic DNA (vii) IMMEDIATE SOURCE:
        (B) CLONE: 121

(ix) FEATURE:
        (A) NAME/KEY: Coding Sequence
        (B) LOCATION: 1..42
        (D) OTHER INFORMATION:/ N at residue 13, 25 and 28 = Inosine (xi) SEQUENCE DESCRIPTION: SEQ ID NO: 2:

CCGGAATTCR CANCCRCAYT CRTCNACNAC CATRTCYTCR TA                             42

(2) INFORMATION FOR SEQ ID NO: 3:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (vii) IMMEDIATE SOURCE:
        (B) CLONE: 136

(ix) FEATURE:
        (B) LOCATION: 1..7
        (D) OTHER INFORMATION: Xaa at residue 4 = Arg or Ser;
            Xaa at residue 6 and 7 = Val, Ile or Met (xi) SEQUENCE DESCRIPTION: SEQ ID NO: 3:

Gly Trp Glu Xaa Trp Xaa Xaa
 1               5

(2) INFORMATION FOR SEQ ID NO: 4:

(i) SEQUENCE CHARACTERISTICS:
        (A) LENGTH: 11 amino acids
        (B) TYPE: amino acid
        (D) TOPOLOGY: linear

```
    (ii) MOLECULE TYPE: peptide (vii) IMMEDIATE SOURCE:
         (B) CLONE: 121

(xi) SEQUENCE DESCRIPTION: SEQ ID NO: 4:

Tyr Glu Asp Met Val Val Asp Glu Cys Gly Cys
 1               5                   10
```

(2) INFORMATION FOR SEQ ID NO: 5:

```
     (i) SEQUENCE CHARACTERISTICS:
         (A) LENGTH: 35 base pairs
         (B) TYPE: nucleic acid
         (C) STRANDEDNESS: single
         (D) TOPOLOGY: linear (ii) MOLECULE TYPE: Genomic DNA (vii) IMMEDIATE SOURCE:
         (B) CLONE: 141

(ix) FEATURE:
         (A) NAME/KEY: Coding Sequence
         (B) LOCATION: 1..35
         (D) OTHER INFORMATION: N at residue 12, 27, 30 and 33 =
             Inosine (xi) SEQUENCE DESCRIPTION: SEQ ID NO: 5:

CCGGAATTCG GNTGGVANRA YTGGRTNRTN KCNCC                           35
```

(2) INFORMATION FOR SEQ ID NO: 6:

```
     (i) SEQUENCE CHARACTERISTICS:
         (A) LENGTH: 33 base pairs
         (B) TYPE: nucleic acid
         (C) STRANDEDNESS: single
         (D) TOPOLOGY: linear (ii) MOLECULE TYPE: Genomic DNA (vii) IMMEDIATE SOURCE:
         (B) CLONE: 145

(ix) FEATURE:
         (A) NAME/KEY: Coding Sequence
         (B) LOCATION: 1..33
         (D) OTHER INFORMATION: N at residue 13, 19, 25 and 28 =
             Inosine (xi) SEQUENCE DESCRIPTION: SEQ ID NO: 6:

CCGGAATTCR CANSCRCANG MNTCNACNRY CAT                             33
```

(2) INFORMATION FOR SEQ ID NO: 7:

```
     (i) SEQUENCE CHARACTERISTICS:
         (A) LENGTH: 9 amino acids
         (B) TYPE: amino acid
         (D) TOPOLOGY: linear (ii) MOLECULE TYPE: peptide (vii) IMMEDIATE SOURCE:
         (B) CLONE: 141

(ix) FEATURE:
         (B) LOCATION: 1..9
         (D) OTHER INFORMATION: Xaa at residue 3 = His, Gln, Asn,
             Lys, Glu or  Asp; Xaa at residue 4 = Asp or Asn; Xaa
             at residues 6 and 7 = Val, Ile or Met; Xaa at
             residue 8 = Glu or Ser (xi) SEQUENCE DESCRIPTION: SEQ ID NO: 7:
```

```
Gly Trp Xaa Xaa Trp Xaa Xaa Xaa Pro
 1               5
```

(2) INFORMATION FOR SEQ ID NO: 8:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (vii) IMMEDIATE SOURCE:
        (B) CLONE: 145

(ix) FEATURE:
        (B) LOCATION: 1..8
        (D) OTHER INFORMATION: Xaa at residues 2 and 3 = Val, Ile,
            Met, Thr or Ala; Xaa at residue 4 = Asp or Glu; Xaa
            at residue 5 = Ala or Ser; Xaa at residue 7 = Gly,
            Ala, Arg, Asn, Asp, Cys, Glu, Gln, His, ile, Leu,
            Lys, Met, Phe Pro, Ser, Thr, Trp, Tyr, and Val.

(xi) SEQUENCE DESCRIPTION: SEQ ID NO: 8:

```
Met Xaa Xaa Xaa Xaa Cys Xaa Cys
 1               5
```

(2) INFORMATION FOR SEQ ID NO: 9:

(i) SEQUENCE CHARACTERISTICS:
        (A) LENGTH: 2329 base pairs
        (B) TYPE: nucleic acid
        (C) STRANDEDNESS: single
        (D) TOPOLOGY: linear (ii) MOLECULE TYPE: Genomic DNA (vii) IMMEDIATE SOURCE:
        (B) CLONE: GD-5

(ix) FEATURE:
        (A) NAME/KEY: Coding Sequence
        (B) LOCATION: 322...1806

(xi) SEQUENCE DESCRIPTION: SEQ ID NO: 9:

```
TTCAAGCCCT CAGTCAGTTG TGCGGGAGAA AGGGGGCGGT CGGCTTTCTC CTTTCAAGAA      60

CGAGTTATTT TCAGCTGCTG ACTGGAGACG GTGCACGTCT GGACACGGGA GCACTTCCAC     120

TATGGGACTG GATACAGACA CACGCCCGGC GGACTTCAAG ACACTCAGAC TGAGGAGAAA     180

GCCCTGCCTG CTGCTGCTGC TGCTGCTGCT GCCACCGCTG CCTCTGAAGA CCCACTCCTT     240

TCATGGTTTT TCCTGCCAAG CCAGAGGCAC CTTCGCTGCT ACGGCCTTTC TCTGTGGTGT     300

CATTCAGCGG CTGGCCAGAG G ATG AGA CTC CCC AAA CTC CTC ACT CTT TTG      351
                       Met Arg Leu Pro Lys Leu Leu Thr Leu Leu
                         1               5                  10

CTG TGG CAC CTG GCT TGG CTG GAC CTG GAA CTC ATC TGC ACT GTG CTG      399
Leu Trp His Leu Ala Trp Leu Asp Leu Glu Leu Ile Cys Thr Val Leu
             15                  20                  25

GGT GCC CCT GAC TTA GGA CAG AGA ACC CCA GGG GCC AAG CCA GGG TTG      447
Gly Ala Pro Asp Leu Gly Gln Arg Thr Pro Gly Ala Lys Pro Gly Leu
         30                  35                  40

ACC AAA GCG GAG GCC AAG GAG AGG CCA CCC CTG GCC AGG AAT GTC TTT      495
Thr Lys Ala Glu Ala Lys Glu Arg Pro Pro Leu Ala Arg Asn Val Phe
     45                  50                  55

AGG CCA GGG GGT CAT ATC TAT GGT GTG GGG GCC ACC AAT GCC AGG GCC      543
Arg Pro Gly Gly His Ile Tyr Gly Val Gly Ala Thr Asn Ala Arg Ala
 60                  65                  70
```

|  |  |
|---|---:|
| AAG GGA AGC TCT GGG CAG ACA CAG GCC AAG AAG GAT GAA CCC AGA AAG<br>Lys Gly Ser Ser Gly Gln Thr Gln Ala Lys Lys Asp Glu Pro Arg Lys<br>75                             80                        85                        90 | 591 |
| ATG CCC CCC AGA TCC GGT GGC TCT GAA ACC AAG CCA GGA CCC TCT TCC<br>Met Pro Pro Arg Ser Gly Gly Ser Glu Thr Lys Pro Gly Pro Ser Ser<br>                            95                              100                        105 | 639 |
| CAG ACT AGA CAG GCT GCA GCC CGG ACT GTA ACC CCA AAA GGA CAG CTT<br>Gln Thr Arg Gln Ala Ala Ala Arg Thr Val Thr Pro Lys Gly Gln Leu<br>                  110                            115                        120 | 687 |
| CCT GGG GGC AAA GCA TCT TCA AAA GCA GGA TCT GCC CCC AGC TCC TTC<br>Pro Gly Gly Lys Ala Ser Ser Lys Ala Gly Ser Ala Pro Ser Ser Phe<br>                125                            130                        135 | 735 |
| CTG CTG AAG AAG ACC AGG GAG CCT GGG ACC CCT CGA GAG CCC AAG GAG<br>Leu Leu Lys Lys Thr Arg Glu Pro Gly Thr Pro Arg Glu Pro Lys Glu<br>      140                            145                        150 | 783 |
| CCG TTC CGC CCG CCC CCC ATC ACA CCC CAC GAA TAC ATG CTC TCC CTG<br>Pro Phe Arg Pro Pro Pro Ile Thr Pro His Glu Tyr Met Leu Ser Leu<br>155                           160                        165                        170 | 831 |
| TAC AGG ACG CTG TCC GAT GCT GAC AGA AAG GGA GGT AAC AGC AGC GTG<br>Tyr Arg Thr Leu Ser Asp Ala Asp Arg Lys Gly Gly Asn Ser Ser Val<br>                175                            180                        185 | 879 |
| AAG TTG GAG GCT GGC CTG GCC AAC ACC ATC ACC AGC TTT ATT GAC AAA<br>Lys Leu Glu Ala Gly Leu Ala Asn Thr Ile Thr Ser Phe Ile Asp Lys<br>      190                            195                        200 | 927 |
| GGG CAA GAT GAC CGA GGC CCT GCG GTC AGG AAG CAG AGG TAC GTG TTT<br>Gly Gln Asp Asp Arg Gly Pro Ala Val Arg Lys Gln Arg Tyr Val Phe<br>                205                            210                        215 | 975 |
| GAC ATC AGT GCC TTG GAG AAG GAT GGG CTG TTG GGG GCT GAA CTG CGG<br>Asp Ile Ser Ala Leu Glu Lys Asp Gly Leu Leu Gly Ala Glu Leu Arg<br>220                           225                        230 | 1023 |
| ATC TTA CGG AAG AAG CCC TTG GAC GTG GCC AAG CCA GCG GTC CCC AGT<br>Ile Leu Arg Lys Lys Pro Leu Asp Val Ala Lys Pro Ala Val Pro Ser<br>235                         240                        245                        250 | 1071 |
| AGC GGG CGG GTT GCC CAA CTG AAG CTG TCC AGC TGC CCC AGC GGC CGG<br>Ser Gly Arg Val Ala Gln Leu Lys Leu Ser Ser Cys Pro Ser Gly Arg<br>                255                            260                        265 | 1119 |
| CAG CCG GCA GCC TTG CTG GAT GTG CGC TCC GTG CCA GGC CTG GAT GGA<br>Gln Pro Ala Ala Leu Leu Asp Val Arg Ser Val Pro Gly Leu Asp Gly<br>                  270                          275                        280 | 1167 |
| TCT GGC TGG GAG GTG TTC GAC ATC TGG AAG CTC TTC CGA AAT TTT AAG<br>Ser Gly Trp Glu Val Phe Asp Ile Trp Lys Leu Phe Arg Asn Phe Lys<br>            285                            290                        295 | 1215 |
| AAC TCA GCG CAG CTG TGC CTG GAG CTG GAG GCC TGG GAA CGG GGC CGG<br>Asn Ser Ala Gln Leu Cys Leu Glu Leu Glu Ala Trp Glu Arg Gly Arg<br>300                           305                        310 | 1263 |
| GCC GTG GAC CTC CGT GGC CTG GGC TTT GAA CGC ACT GCC CGA CAG GTC<br>Ala Val Asp Leu Arg Gly Leu Gly Phe Glu Arg Thr Ala Arg Gln Val<br>315                         320                        325                        330 | 1311 |
| CAC GAG AAA GCC TTG TTC CTA GTG TTT GGT CGT ACC AAG AAA CGG GAC<br>His Glu Lys Ala Leu Phe Leu Val Phe Gly Arg Thr Lys Lys Arg Asp<br>                335                            340                        345 | 1359 |
| CTG TTC TTT AAT GAG ATT AAG GCC CGC TCT GGC CAG GAT GAC AAG ACT<br>Leu Phe Phe Asn Glu Ile Lys Ala Arg Ser Gly Gln Asp Asp Lys Thr<br>                  350                          355                        360 | 1407 |
| GTG TAT GAA TAT TTG TTC AGC CAG CGG CGG AAA CGC CGG GCC CCA TTG<br>Val Tyr Glu Tyr Leu Phe Ser Gln Arg Arg Lys Arg Arg Ala Pro Leu<br>              365                          370                        375 | 1455 |
| GCC AAT CGC CAG GGC AAG CGA CCC AGC AAG AAC CTC AAG GCT CGC TGC<br>Ala Asn Arg Gln Gly Lys Arg Pro Ser Lys Asn Leu Lys Ala Arg Cys | 1503 |

```
                    380              385              390
AGT CGC AAG GCC TTG CAT GTC AAC TTC AAG GAC ATG GGC TGG GAC GAC    1551
Ser Arg Lys Ala Leu His Val Asn Phe Lys Asp Met Gly Trp Asp Asp
395                 400              405              410

TGG ATC ATC GCA CCT CTT GAG TAT GAG GCC TTC CAC TGC GAA GGA CTG    1599
Trp Ile Ile Ala Pro Leu Glu Tyr Glu Ala Phe His Cys Glu Gly Leu
                    415              420              425

TGT GAG TTC CCC TTG CGC TCC CAC TTG GAG CCC ACA AAC CAC GCA GTC    1647
Cys Glu Phe Pro Leu Arg Ser His Leu Glu Pro Thr Asn His Ala Val
                430              435              440

ATT CAG ACC CTA ATG AAC TCT ATG GAC CCT GAA TCC ACA CCA CCC ACT    1695
Ile Gln Thr Leu Met Asn Ser Met Asp Pro Glu Ser Thr Pro Pro Thr
                445              450              455

TGT TGT GTG CCT ACA CGG CTG AGT CCT ATT AGC ATC CTC TTC ATC GAC    1743
Cys Cys Val Pro Thr Arg Leu Ser Pro Ile Ser Ile Leu Phe Ile Asp
            460              465              470

TCT GCC AAC AAC GTG GTG TAT AAA CAG TAC GAG GAC ATG GTC GTG GAA    1791
Ser Ala Asn Asn Val Val Tyr Lys Gln Tyr Glu Asp Met Val Val Glu
475             480              485              490

TCT TGT GGC TGC AGG TAGCAGCACC GGCCCACCTG TCTTCCAGGG TGGCACATC  A  1847
Ser Cys Gly Cys Arg
            495

GAGACTACCC CCTCTACAGG TTCCTGGAGT AACAGAGAGC CTGTGAAGCT GCTGCCCGAA    1907

GTTTCCTGGC AGCCTGCAGG AAAGAGTTCT CAGCAGGCTT ACTCTCTGGA TGTGATCTGG    1967

ACTAAAGAGA TCACCTTCTG AAGATTCCTG CCCAAGGAAC AGACTCTGAG TGGGCCTGGG    2027

GCTCAGGAAA GGTGTTCTTA ATGAGATTCA GTTCACCATC TCTCCTGCCG GGGCCGGAGA    2087

CCTTCATTTC TCTCCAGACT CTCCAGAGAA GTTGTAGCTA TATCCTAAGC TCTTTAAGGG    2147

AGAGCTGTCT CCTCCTTGAA TCACCTTTGT GCCTGGTGAC TTTCTGCCAC GAGATGTTCA    2207

TTACAGGGGC TGGGCAAAGA AGGGGAAAGG GCTTGGGCAG GGGTGAAGAG AAGAGTATGA    2267

GCCTAATTAG ACTGTTAGAT TAAAATGTAC ATCGATGACA TAAAAGCTGA ATCTTCATGG    2327

CT                                                                  2329

(2) INFORMATION FOR SEQ ID NO: 10:

(i) SEQUENCE CHARACTERISTICS:
        (A) LENGTH: 495 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 10:

Met Arg Leu Pro Lys Leu Leu Thr Leu Leu Trp His Leu Ala Trp
 1               5                  10                  15

Leu Asp Leu Glu Leu Ile Cys Thr Val Leu Gly Ala Pro Asp Leu Gly
                20                  25                  30

Gln Arg Thr Pro Gly Ala Lys Pro Gly Leu Thr Lys Ala Glu Ala Lys
            35                  40                  45

Glu Arg Pro Pro Leu Ala Arg Asn Val Phe Arg Pro Gly Gly His Ile
        50                  55                  60

Tyr Gly Val Gly Ala Thr Asn Ala Arg Ala Lys Gly Ser Ser Gly Gln
65                  70                  75                  80

Thr Gln Ala Lys Lys Asp Glu Pro Arg Lys Met Pro Pro Arg Ser Gly
                85                  90                  95
```

-continued

```
Gly Ser Glu Thr Lys Pro Gly Pro Ser Ser Gln Thr Arg Gln Ala Ala
            100                 105                 110

Ala Arg Thr Val Thr Pro Lys Gly Gln Leu Pro Gly Gly Lys Ala Ser
            115                 120                 125

Ser Lys Ala Gly Ser Ala Pro Ser Ser Phe Leu Leu Lys Lys Thr Arg
            130                 135                 140

Glu Pro Gly Thr Pro Arg Glu Pro Lys Glu Pro Phe Arg Pro Pro Pro
145                 150                 155                 160

Ile Thr Pro His Glu Tyr Met Leu Ser Leu Tyr Arg Thr Leu Ser Asp
                165                 170                 175

Ala Asp Arg Lys Gly Gly Asn Ser Ser Val Lys Leu Glu Ala Gly Leu
                180                 185                 190

Ala Asn Thr Ile Thr Ser Phe Ile Asp Lys Gly Gln Asp Asp Arg Gly
                195                 200                 205

Pro Ala Val Arg Lys Gln Arg Tyr Val Phe Asp Ile Ser Ala Leu Glu
            210                 215                 220

Lys Asp Gly Leu Leu Gly Ala Glu Leu Arg Ile Leu Arg Lys Lys Pro
225                 230                 235                 240

Leu Asp Val Ala Lys Pro Ala Val Pro Ser Ser Gly Arg Val Ala Gln
                245                 250                 255

Leu Lys Leu Ser Ser Cys Pro Ser Gly Arg Gln Pro Ala Ala Leu Leu
            260                 265                 270

Asp Val Arg Ser Val Pro Gly Leu Asp Gly Ser Gly Trp Glu Val Phe
            275                 280                 285

Asp Ile Trp Lys Leu Phe Arg Asn Phe Lys Asn Ser Ala Gln Leu Cys
290                 295                 300

Leu Glu Leu Glu Ala Trp Glu Arg Gly Arg Ala Val Asp Leu Arg Gly
305                 310                 315                 320

Leu Gly Phe Glu Arg Thr Ala Arg Gln Val His Glu Lys Ala Leu Phe
                325                 330                 335

Leu Val Phe Gly Arg Thr Lys Lys Arg Asp Leu Phe Phe Asn Glu Ile
                340                 345                 350

Lys Ala Arg Ser Gly Gln Asp Asp Lys Thr Val Tyr Glu Tyr Leu Phe
            355                 360                 365

Ser Gln Arg Arg Lys Arg Arg Ala Pro Leu Ala Asn Arg Gln Gly Lys
            370                 375                 380

Arg Pro Ser Lys Asn Leu Lys Ala Arg Cys Ser Arg Lys Ala Leu His
385                 390                 395                 400

Val Asn Phe Lys Asp Met Gly Trp Asp Asp Trp Ile Ile Ala Pro Leu
                405                 410                 415

Glu Tyr Glu Ala Phe His Cys Glu Gly Leu Cys Glu Phe Pro Leu Arg
                420                 425                 430

Ser His Leu Glu Pro Thr Asn His Ala Val Ile Gln Thr Leu Met Asn
            435                 440                 445

Ser Met Asp Pro Glu Ser Thr Pro Pro Thr Cys Cys Val Pro Thr Arg
450                 455                 460

Leu Ser Pro Ile Ser Ile Leu Phe Ile Asp Ser Ala Asn Asn Val Val
465                 470                 475                 480

Tyr Lys Gln Tyr Glu Asp Met Val Val Glu Ser Cys Gly Cys Arg
                485                 490                 495
```

(2) INFORMATION FOR SEQ ID NO: 11:

(i) SEQUENCE CHARACTERISTICS:
    (A) LENGTH: 124 amino acids
    (B) TYPE: amino acid
    (D) TOPOLOGY: linear (ii) MOLECULE TYPE: protein (vii) IMMEDIATE SOURCE:
    (B) CLONE: GDF-1

(xi) SEQUENCE DESCRIPTION: SEQ ID NO: 11:

```
Arg Leu Arg Arg His Thr Glu Pro Arg Val Glu Val Gly Pro Val Gly
 1               5                  10                  15

Thr Cys Arg Thr Arg Arg Leu His Val Ser Phe Arg Glu Val Gly Trp
             20                  25                  30

His Arg Trp Val Ile Ala Pro Arg Gly Phe Leu Ala Asn Phe Cys Gln
         35                  40                  45

Gly Thr Cys Ala Leu Pro Glu Thr Leu Arg Gly Pro Gly Pro Pro
     50                  55                  60

Ala Leu Asn His Ala Val Leu Arg Ala Leu Met His Ala Ala Ala Pro
 65                  70                  75                  80

Thr Pro Gly Ala Gly Ser Pro Cys Cys Val Pro Glu Arg Leu Ser Pro
                 85                  90                  95

Ile Ser Val Leu Phe Phe Asp Asn Glu Asp Asn Val Val Leu Arg His
                100                 105                 110

Tyr Glu Asp Met Val Val Asp Glu Cys Gly Cys Arg
            115                 120
```

(2) INFORMATION FOR SEQ ID NO: 12:

(i) SEQUENCE CHARACTERISTICS:
    (A) LENGTH: 118 amino acids
    (B) TYPE: amino acid
    (D) TOPOLOGY: linear (ii) MOLECULE TYPE: protein (vii) IMMEDIATE SOURCE:
    (B) CLONE: GDF-3

(xi) SEQUENCE DESCRIPTION: SEQ ID NO: 12:

```
Arg Lys Arg Arg Ala Ala Ile Ser Val Pro Lys Gly Phe Cys Arg Asn
 1               5                  10                  15

Phe Cys His Arg His Gln Leu Phe Ile Asn Phe Gln Asp Leu Gly Trp
             20                  25                  30

His Lys Trp Val Ile Ala Pro Lys Gly Phe Met Ala Asn Tyr Cys His
         35                  40                  45

Gly Glu Cys Pro Phe Ser Met Thr Thr Tyr Leu Asn Ser Ser Asn Tyr
     50                  55                  60

Ala Phe Met Gln Ala Leu Met His Met Ala Asp Pro Lys Val Pro Lys
 65                  70                  75                  80

Ala Val Cys Val Pro Thr Lys Leu Ser Pro Ile Ser Met Leu Tyr Gln
                 85                  90                  95

Asp Ser Asp Lys Asn Val Ile Leu Arg His Tyr Glu Asp Met Val Val
                100                 105                 110

Asp Glu Cys Gly Cys Gly
            115
```

(2) INFORMATION FOR SEQ ID NO: 13:

(i) SEQUENCE CHARACTERISTICS:

(A) LENGTH: 119 amino acids
            (B) TYPE: amino acid
            (D) TOPOLOGY: linear (ii) MOLECULE TYPE: protein (vii) IMMEDIATE SOURCE:
            (B) CLONE: GDF-5

(xi) SEQUENCE DESCRIPTION: SEQ ID NO: 13:

Pro Leu Ala Asn Arg Gln Gly Lys Arg Pro Ser Lys Asn Leu Lys Ala
 1               5                  10                  15

Arg Cys Ser Arg Lys Ala Leu His Val Asn Phe Lys Asp Met Gly Trp
            20                  25                  30

Asp Asp Trp Ile Ile Ala Pro Leu Glu Tyr Glu Ala Phe His Cys Glu
        35                  40                  45

Gly Leu Cys Glu Phe Pro Leu Arg Ser His Leu Glu Pro Thr Asn His
    50                  55                  60

Ala Val Ile Gln Thr Leu Met Asn Ser Met Asp Pro Glu Ser Thr Pro
65                  70                  75                  80

Pro Thr Cys Cys Val Pro Thr Arg Leu Ser Pro Ile Ser Ile Leu Phe
                85                  90                  95

Ile Asp Ser Ala Asn Asn Val Val Tyr Lys Gln Tyr Glu Asp Met Val
            100                 105                 110

Val Glu Ser Cys Gly Cys Arg
            115

(2) INFORMATION FOR SEQ ID NO: 14:

(i) SEQUENCE CHARACTERISTICS:
            (A) LENGTH: 119 amino acids
            (B) TYPE: amino acid
            (D) TOPOLOGY: linear (ii) MOLECULE TYPE: protein (vii) IMMEDIATE SOURCE:
            (B) CLONE: GDF-9

(xi) SEQUENCE DESCRIPTION: SEQ ID NO: 14:

Ser Phe Asn Leu Ser Glu Tyr Phe Lys Gln Phe Leu Phe Pro Gln Asn
 1               5                  10                  15

Glu Cys Glu Leu His Asp Phe Arg Leu Ser Phe Ser Gln Leu Lys Trp
            20                  25                  30

Asp Asn Trp Ile Val Ala Pro His Arg Tyr Asn Pro Arg Tyr Cys Lys
        35                  40                  45

Gly Asp Cys Pro Arg Ala Val Arg His Arg Tyr Gly Ser Pro Val His
    50                  55                  60

Thr Met Val Gln Asn Ile Ile Tyr Glu Lys Leu Asp Pro Ser Val Pro
65                  70                  75                  80

Arg Pro Ser Cys Val Pro Gly Lys Tyr Ser Pro Leu Ser Val Leu Thr
                85                  90                  95

Ile Glu Pro Asp Gly Ser Ile Ala Tyr Lys Glu Tyr Glu Asp Met Ile
            100                 105                 110

Ala Thr Arg Cys Thr Cys Arg
            115

(2) INFORMATION FOR SEQ ID NO: 15:

(i) SEQUENCE CHARACTERISTICS:
            (A) LENGTH: 118 amino acids

-continued (B) TYPE: amino acid
   (D) TOPOLOGY: linear (ii) MOLECULE TYPE: protein (vii) IMMEDIATE SOURCE:
   (B) CLONE: BMP-2

(xi) SEQUENCE DESCRIPTION: SEQ ID NO: 15:

```
Arg Glu Lys Arg Gln Ala Lys His Lys Gln Arg Lys Arg Leu Lys Ser
 1               5                  10                  15

Ser Cys Lys Arg His Pro Leu Tyr Val Asp Phe Ser Asp Val Gly Trp
                20                  25                  30

Asn Asp Trp Ile Val Ala Pro Pro Gly Tyr His Ala Phe Tyr Cys His
            35                  40                  45

Gly Glu Cys Pro Phe Pro Leu Ala Asp His Leu Asn Ser Thr Asn His
        50                  55                  60

Ala Ile Val Gln Thr Leu Val Asn Ser Val Asn Ser Lys Ile Pro Lys
65                  70                  75                  80

Ala Cys Cys Val Pro Thr Glu Leu Ser Ala Ile Ser Met Leu Tyr Leu
                85                  90                  95

Asp Glu Asn Glu Lys Val Val Leu Lys Asn Tyr Gln Asp Met Val Val
               100                 105                 110

Glu Gly Cys Gly Cys Arg
               115
```

(2) INFORMATION FOR SEQ ID NO: 16:

(i) SEQUENCE CHARACTERISTICS:
   (A) LENGTH: 118 amino acids
   (B) TYPE: amino acid
   (D) TOPOLOGY: linear (ii) MOLECULE TYPE: protein (vii) IMMEDIATE SOURCE:
   (B) CLONE: BMP-4

(xi) SEQUENCE DESCRIPTION: SEQ ID NO: 16:

```
Lys Arg Ser Pro Lys His His Ser Gln Arg Ala Arg Lys Lys Asn Lys
 1               5                  10                  15

Asn Cys Arg Arg His Ser Leu Tyr Val Asp Phe Ser Asp Val Gly Trp
                20                  25                  30

Asn Asp Trp Ile Val Ala Pro Pro Gly Tyr Gln Ala Phe Tyr Cys His
            35                  40                  45

Gly Asp Cys Pro Phe Pro Leu Ala Asp His Leu Asn Ser Thr Asn His
        50                  55                  60

Ala Ile Val Gln Thr Leu Val Asn Ser Val Asn Ser Ser Ile Pro Lys
65                  70                  75                  80

Ala Cys Cys Val Pro Thr Glu Leu Ser Ala Ile Ser Met Leu Tyr Leu
                85                  90                  95

Asp Glu Tyr Asp Lys Val Val Leu Lys Asn Tyr Gln Glu Met Val Val
               100                 105                 110

Glu Gly Cys Gly Cys Arg
               115
```

(2) INFORMATION FOR SEQ ID NO: 17:

(i) SEQUENCE CHARACTERISTICS:
   (A) LENGTH: 119 amino acids
   (B) TYPE: amino acid (D) TOPOLOGY: linear (ii) MOLECULE TYPE: protein (vii) IMMEDIATE SOURCE:
(B) CLONE: Vgr-1

(xi) SEQUENCE DESCRIPTION: SEQ ID NO: 17:

```
Ser Arg Gly Ser Gly Ser Ser Asp Tyr Asn Gly Ser Glu Leu Lys Thr
 1               5                  10                  15
Ala Cys Lys Lys His Glu Leu Tyr Val Ser Phe Gln Asp Leu Gly Trp
            20                  25                  30
Gln Asp Trp Ile Ile Ala Pro Lys Gly Tyr Ala Ala Asn Tyr Cys Asp
        35                  40                  45
Gly Glu Cys Ser Phe Pro Leu Asn Ala His Met Asn Ala Thr Asn His
 50                  55                  60
Ala Ile Val Gln Thr Leu Val His Leu Met Asn Pro Glu Tyr Val Pro
 65                  70                  75                  80
Lys Pro Cys Cys Ala Pro Thr Lys Leu Asn Ala Ile Ser Val Leu Tyr
                85                  90                  95
Phe Asp Asp Asn Ser Asn Val Ile Leu Lys Lys Tyr Arg Asn Met Val
            100                 105                 110
Val Arg Ala Cys Gly Cys His
            115
```

(2) INFORMATION FOR SEQ ID NO: 18:

(i) SEQUENCE CHARACTERISTICS:
(A) LENGTH: 119 amino acids
(B) TYPE: amino acid
(D) TOPOLOGY: linear (ii) MOLECULE TYPE: protein (vii) IMMEDIATE SOURCE:
(B) CLONE: OP-1

(xi) SEQUENCE DESCRIPTION: SEQ ID NO: 18:

```
Leu Arg Met Ala Asn Val Ala Glu Asn Ser Ser Asp Gln Arg Gln
 1               5                  10                  15
Ala Cys Lys Lys His Glu Leu Tyr Val Ser Phe Arg Asp Leu Gly Trp
            20                  25                  30
Gln Asp Trp Ile Ile Ala Pro Glu Gly Tyr Ala Ala Tyr Tyr Cys Glu
        35                  40                  45
Gly Glu Cys Ala Phe Pro Leu Asn Ser Tyr Met Asn Ala Thr Asn His
 50                  55                  60
Ala Ile Val Gln Thr Leu Val His Phe Ile Asn Pro Glu Thr Val Pro
 65                  70                  75                  80
Lys Pro Cys Cys Ala Pro Thr Gln Leu Asn Ala Ile Ser Val Leu Tyr
                85                  90                  95
Phe Asp Asp Ser Ser Asn Val Ile Leu Lys Lys Tyr Arg Asn Met Val
            100                 105                 110
Val Arg Ala Cys Gly Cys His
            115
```

(2) INFORMATION FOR SEQ ID NO: 19:

(i) SEQUENCE CHARACTERISTICS:
(A) LENGTH: 119 amino acids
(B) TYPE: amino acid
(D) TOPOLOGY: linear (ii) MOLECULE TYPE: protein (vii) IMMEDIATE SOURCE:
    (B) CLONE: BMP-5

(xi) SEQUENCE DESCRIPTION: SEQ ID NO: 19:

Ser Arg Met Ser Ser Val Gly Asp Tyr Asn Thr Ser Glu Gln Lys Gln
 1               5                  10                  15

Ala Cys Lys Lys His Glu Leu Tyr Val Ser Phe Arg Asp Leu Gly Trp
            20                  25                  30

Gln Asp Trp Ile Ile Ala Pro Glu Gly Tyr Ala Ala Phe Tyr Cys Asp
        35                  40                  45

Gly Glu Cys Ser Phe Pro Leu Asn Ala His Met Asn Ala Thr Asn His
    50                  55                  60

Ala Ile Val Gln Thr Leu Val His Leu Met Phe Pro Asp His Val Pro
65                  70                  75                  80

Lys Pro Cys Cys Ala Pro Thr Lys Leu Asn Ala Ile Ser Val Leu Tyr
                85                  90                  95

Phe Asp Asp Ser Ser Asn Val Ile Leu Lys Lys Tyr Arg Asn Met Val
            100                 105                 110

Val Arg Ser Cys Gly Cys His
            115

(2) INFORMATION FOR SEQ ID NO: 20:

(i) SEQUENCE CHARACTERISTICS:
        (A) LENGTH: 120 amino acids
        (B) TYPE: amino acid
        (D) TOPOLOGY: linear (ii) MOLECULE TYPE: protein (vii) IMMEDIATE SOURCE:
        (B) CLONE: BMP-3

(xi) SEQUENCE DESCRIPTION: SEQ ID NO: 20:

Glu Gln Thr Leu Lys Lys Ala Arg Arg Lys Gln Trp Ile Glu Pro Arg
 1               5                  10                  15

Asn Cys Ala Arg Arg Tyr Leu Lys Val Asp Phe Ala Asp Ile Gly Trp
            20                  25                  30

Ser Glu Trp Ile Ile Ser Pro Lys Ser Phe Asp Ala Tyr Tyr Cys Ser
        35                  40                  45

Gly Ala Cys Gln Phe Pro Met Pro Lys Ser Leu Lys Pro Ser Asn His
    50                  55                  60

Ala Thr Ile Gln Ser Ile Val Arg Ala Val Gly Val Val Pro Gly Ile
65                  70                  75                  80

Pro Glu Pro Cys Cys Val Pro Glu Lys Met Ser Ser Leu Ser Ile Leu
                85                  90                  95

Phe Phe Asp Glu Asn Lys Asn Val Val Leu Lys Val Tyr Pro Asn Met
            100                 105                 110

Thr Val Glu Ser Cys Ala Cys Arg
            115                 120

(2) INFORMATION FOR SEQ ID NO: 21:

(i) SEQUENCE CHARACTERISTICS:
        (A) LENGTH: 116 amino acids
        (B) TYPE: amino acid
        (D) TOPOLOGY: linear (ii) MOLECULE TYPE: protein (vii) IMMEDIATE SOURCE:
    (B) CLONE: MIS (xi) SEQUENCE DESCRIPTION: SEQ ID NO: 21:

```
Gly Pro Gly Arg Ala Gln Arg Ser Ala Gly Ala Thr Ala Ala Asp Gly
 1               5                  10                  15

Pro Cys Ala Leu Arg Glu Leu Ser Val Asp Leu Arg Ala Glu Arg Ser
             20                  25                  30

Val Leu Ile Pro Glu Thr Tyr Gln Ala Asn Asn Cys Gln Gly Val Cys
         35                  40                  45

Gly Trp Pro Gln Ser Asp Arg Asn Pro Arg Tyr Gly Asn His Val Val
     50                  55                  60

Leu Leu Leu Lys Met Gln Ala Arg Gly Ala Ala Leu Ala Arg Pro Pro
 65                  70                  75                  80

Cys Cys Val Pro Thr Ala Tyr Ala Gly Lys Leu Leu Ile Ser Leu Ser
             85                  90                  95

Glu Glu Arg Ile Ser Ala His His Val Pro Asn Met Val Ala Thr Glu
            100                 105                 110

Cys Gly Cys Arg
            115
```

(2) INFORMATION FOR SEQ ID NO: 22:

(i) SEQUENCE CHARACTERISTICS:
    (A) LENGTH: 122 amino acids
    (B) TYPE: amino acid
    (D) TOPOLOGY: linear (ii) MOLECULE TYPE: protein (vii) IMMEDIATE SOURCE:
    (B) CLONE: Inhibit-alpha (xi) SEQUENCE DESCRIPTION: SEQ ID NO: 22:

```
Ala Leu Arg Leu Leu Gln Arg Pro Pro Glu Glu Pro Ala Ala His Ala
 1               5                  10                  15

Asn Cys His Arg Val Ala Leu Asn Ile Ser Phe Gln Glu Leu Gly Trp
             20                  25                  30

Glu Arg Trp Ile Val Tyr Pro Pro Ser Phe Ile Phe His Tyr Cys His
         35                  40                  45

Gly Gly Cys Gly Leu His Ile Pro Pro Asn Leu Ser Leu Pro Val Pro
     50                  55                  60

Gly Ala Pro Pro Thr Pro Ala Gln Pro Tyr Ser Leu Leu Pro Gly Ala
 65                  70                  75                  80

Gln Pro Cys Cys Ala Ala Leu Pro Gly Thr Met Arg Pro Leu His Val
             85                  90                  95

Arg Thr Thr Ser Asp Gly Gly Tyr Ser Phe Lys Tyr Glu Thr Val Pro
            100                 105                 110

Asn Leu Leu Thr Gln His Cys Ala Cys Ile
            115                 120
```

(2) INFORMATION FOR SEQ ID NO: 23:

(i) SEQUENCE CHARACTERISTICS:
    (A) LENGTH: 122 amino acids
    (B) TYPE: amino acid
    (D) TOPOLOGY: linear (ii) MOLECULE TYPE: protein (vii) IMMEDIATE SOURCE:
    (B) CLONE: Inhibit-beta-alpha (xi) SEQUENCE DESCRIPTION: SEQ ID NO: 23:

```
His Arg Arg Arg Arg Gly Leu Glu Cys Asp Gly Lys Val Asn Ile
 1               5                  10                  15

Cys Cys Lys Lys Gln Phe Phe Val Ser Phe Lys Asp Ile Gly Trp Asn
                20                  25                  30

Asp Trp Ile Ile Ala Pro Ser Gly Tyr His Ala Asn Tyr Cys Glu Gly
                35                  40                  45

Glu Cys Pro Ser His Ile Ala Gly Thr Ser Gly Ser Ser Leu Ser Phe
     50                  55                  60

His Ser Thr Val Ile Asn His Tyr Arg Met Arg Gly His Ser Pro Phe
 65                  70                  75                  80

Ala Asn Leu Lys Ser Cys Cys Val Pro Thr Lys Leu Arg Pro Met Ser
                85                  90                  95

Met Leu Tyr Tyr Asp Asp Gly Gln Asn Ile Ile Lys Lys Asp Ile Gln
                100                 105                 110

Asn Met Ile Val Glu Glu Cys Gly Cys Ser
            115                 120
```

(2) INFORMATION FOR SEQ ID NO: 24:

(i) SEQUENCE CHARACTERISTICS:
        (A) LENGTH: 121 amino acids
        (B) TYPE: amino acid
        (D) TOPOLOGY: linear (ii) MOLECULE TYPE: protein (vii) IMMEDIATE SOURCE:
        (B) CLONE: Inhibit-beta-beta (xi) SEQUENCE DESCRIPTION: SEQ ID NO: 24:

```
His Arg Ile Arg Lys Arg Gly Leu Glu Cys Asp Gly Arg Thr Asn Leu
 1               5                  10                  15

Cys Cys Arg Gln Gln Phe Phe Ile Asp Phe Arg Leu Ile Gly Trp Asn
                20                  25                  30

Asp Trp Ile Ile Ala Pro Thr Gly Tyr Tyr Gly Asn Tyr Cys Glu Gly
                35                  40                  45

Ser Cys Pro Ala Tyr Leu Ala Gly Val Pro Gly Ser Ala Ser Ser Phe
     50                  55                  60

His Thr Ala Val Val Asn Gln Tyr Arg Met Arg Gly Leu Asn Pro Gly
 65                  70                  75                  80

Thr Val Asn Ser Cys Cys Ile Pro Thr Lys Leu Ser Thr Met Ser Met
                85                  90                  95

Leu Tyr Phe Asp Asp Glu Tyr Asn Ile Val Lys Arg Asp Val Pro Asn
                100                 105                 110

Met Ile Val Glu Glu Cys Gly Cys Ala
            115                 120
```

(2) INFORMATION FOR SEQ ID NO: 25:

(i) SEQUENCE CHARACTERISTICS:
        (A) LENGTH: 115 amino acids
        (B) TYPE: amino acid
        (D) TOPOLOGY: linear (ii) MOLECULE TYPE: protein (vii) IMMEDIATE SOURCE:
    (B) CLONE: TGF-beta-1

(xi) SEQUENCE DESCRIPTION: SEQ ID NO: 25:

```
His Arg Arg Ala Leu Asp Thr Asn Tyr Cys Phe Ser Ser Thr Glu Lys
 1               5                  10                  15

Asn Cys Cys Val Arg Gln Leu Tyr Ile Asp Phe Arg Lys Asp Leu Gly
                20                  25                  30

Trp Lys Trp Ile His Glu Pro Lys Gly Tyr His Ala Asn Phe Cys Leu
            35                  40                  45

Gly Pro Cys Pro Tyr Ile Trp Ser Leu Asp Thr Gln Tyr Ser Lys Val
        50                  55                  60

Leu Ala Leu Tyr Asn Gln His Asn Pro Gly Ala Ser Ala Ala Pro Cys
65                  70                  75                  80

Cys Val Pro Gln Ala Leu Glu Pro Leu Pro Ile Val Tyr Tyr Val Gly
                85                  90                  95

Arg Lys Pro Lys Val Glu Gln Leu Ser Asn Met Ile Val Arg Ser Cys
                100                 105                 110

Lys Cys Ser
        115
```

(2) INFORMATION FOR SEQ ID NO: 26:

(i) SEQUENCE CHARACTERISTICS:
        (A) LENGTH: 115 amino acids
        (B) TYPE: amino acid
        (D) TOPOLOGY: linear (ii) MOLECULE TYPE: protein (vii) IMMEDIATE SOURCE:
        (B) CLONE: TGF-beta-2

(xi) SEQUENCE DESCRIPTION: SEQ ID NO: 26:

```
Lys Lys Arg Ala Leu Asp Ala Ala Tyr Cys Phe Arg Asn Val Gln Asp
 1               5                  10                  15

Asn Cys Cys Leu Arg Pro Leu Tyr Ile Asp Phe Lys Arg Asp Leu Gly
                20                  25                  30

Trp Lys Trp Ile His Glu Pro Lys Gly Tyr Asn Ala Asn Phe Cys Ala
            35                  40                  45

Gly Ala Cys Pro Tyr Leu Trp Ser Ser Asp Thr Gln His Ser Arg Val
        50                  55                  60

Leu Ser Leu Tyr Asn Thr Ile Asn Pro Glu Ala Ser Ala Ser Pro Cys
65                  70                  75                  80

Cys Val Ser Gln Asp Leu Glu Pro Leu Thr Ile Leu Tyr Tyr Ile Gly
                85                  90                  95

Lys Thr Pro Lys Ile Glu Gln Leu Ser Asn Met Ile Val Lys Ser Cys
                100                 105                 110

Lys Cys Ser
        115
```

(2) INFORMATION FOR SEQ ID NO: 27:

(i) SEQUENCE CHARACTERISTICS:
        (A) LENGTH: 115 amino acids
        (B) TYPE: amino acid
        (D) TOPOLOGY: linear (ii) MOLECULE TYPE: protein (vii) IMMEDIATE SOURCE:

-continued (B) CLONE: TGF-beta-3

(xi) SEQUENCE DESCRIPTION: SEQ ID NO: 27:

Lys Lys Arg Ala Leu Asp Thr Asn Tyr Cys Phe Arg Asn Leu Glu Glu
1               5                   10                  15

Asn Cys Cys Val Arg Pro Leu Tyr Ile Asp Phe Arg Gln Asp Leu Gly
            20                  25                  30

Trp Lys Trp Val His Glu Pro Lys Gly Tyr Tyr Ala Asn Phe Cys Ser
        35                  40                  45

Gly Pro Cys Pro Tyr Leu Arg Ser Ala Asp Thr Thr His Ser Thr Val
        50                  55                  60

Leu Gly Leu Tyr Asn Thr Leu Asn Pro Glu Ala Ser Ala Ser Pro Cys
65                  70                  75                  80

Cys Val Pro Gln Asp Leu Glu Pro Leu Thr Ile Leu Tyr Tyr Val Gly
                85                  90                  95

Arg Thr Pro Lys Val Glu Gln Leu Ser Asn Met Val Val Lys Ser Cys
            100                 105                 110

Lys Cys Ser
        115

(2) INFORMATION FOR SEQ ID NO: 28:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 28:

Arg Arg Lys Arg Arg
1               5